United States Patent
Bruchman et al.

(10) Patent No.: US 12,133,795 B2
(45) Date of Patent: Nov. 5, 2024

(54) GEOMETRIC CONTROL OF BENDING CHARACTER IN PROSTHETIC HEART VALVE LEAFLETS

(71) Applicant: Edwards Lifesciences Corporation, Irvine, CA (US)

(72) Inventors: William C. Bruchman, Camp Verde, AZ (US); Cody L. Hartman, Flagstaff, AZ (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 854 days.

(21) Appl. No.: 17/188,333

(22) Filed: Mar. 1, 2021

(65) Prior Publication Data
US 2021/0205074 A1 Jul. 8, 2021

Related U.S. Application Data

(63) Continuation of application No. 13/835,988, filed on Mar. 15, 2013, now Pat. No. 10,966,820.
(Continued)

(51) Int. Cl.
*A61F 2/24* (2006.01)

(52) U.S. Cl.
CPC .......... *A61F 2/2409* (2013.01); *A61F 2/2412* (2013.01); *A61F 2/2415* (2013.01);
(Continued)

(58) Field of Classification Search
CPC .... A61F 2/2409; A61F 2/2412; A61F 2/2415; A61F 2230/0023; A61F 2230/0026; A61F 2240/001
See application file for complete search history.

(56) References Cited

U.S. PATENT DOCUMENTS

| | | |
|---|---|---|
| 654,799 A | 7/1900 | Levett |
| 3,953,566 A | 4/1976 | Gore |

(Continued)

FOREIGN PATENT DOCUMENTS

| | | |
|---|---|---|
| AU | 2013363172 A1 | 7/2015 |
| AU | 2017202405 A1 | 4/2017 |

(Continued)

OTHER PUBLICATIONS

Cardiac Surgery in the Adult, Third Edition, Chapter 2 2008.
(Continued)

*Primary Examiner* — Yashita Sharma
*Assistant Examiner* — Aren Patel
(74) *Attorney, Agent, or Firm* — Julia F. Kottemeier; Klarquist Sparkman LLP

(57) ABSTRACT

Described embodiments are directed toward prosthetic valves having leaflets of particular shapes that control bending character. In accordance with an embodiment, a prosthetic valve has a plurality of leaflets. Each leaflet includes a central region and two side regions on opposite sides of the central region. The central region is defined by a shape of an isosceles triangle defined by two central region sides, the leaflet base and the leaflet free edge, wherein the two central region sides converge from the leaflet base. Each of the two side regions has a shape of a triangle and each is defined by one of the central region sides, one of the leaflet sides, and the leaflet free edge.

20 Claims, 8 Drawing Sheets

Related U.S. Application Data

(60) Provisional application No. 61/739,721, filed on Dec. 19, 2012.

(52) U.S. Cl.
CPC ............... *A61F 2230/0023* (2013.01); *A61F 2230/0026* (2013.01); *A61F 2240/001* (2013.01)

(56) References Cited

U.S. PATENT DOCUMENTS

| | | |
|---|---|---|
| 4,178,639 A | 12/1979 | Bokros |
| 4,187,390 A | 2/1980 | Gore |
| 4,222,126 A | 9/1980 | Boretos et al. |
| 4,265,694 A | 5/1981 | Boretos et al. |
| 4,332,035 A | 6/1982 | Mano |
| 4,340,091 A | 7/1982 | Skelton et al. |
| 4,477,930 A | 10/1984 | Totten et al. |
| 4,556,996 A | 12/1985 | Wallace |
| 4,626,255 A | 12/1986 | Reichart et al. |
| 4,759,759 A | 7/1988 | Walker et al. |
| 4,851,000 A | 7/1989 | Gupta |
| 4,877,661 A | 10/1989 | House et al. |
| 4,955,899 A | 9/1990 | Della et al. |
| 5,026,513 A | 6/1991 | House et al. |
| 5,064,435 A | 11/1991 | Porter |
| 5,071,609 A | 12/1991 | Tu et al. |
| 5,123,918 A | 6/1992 | Perrier et al. |
| 5,163,955 A | 11/1992 | Love et al. |
| 5,415,667 A | 5/1995 | Frater |
| 5,469,868 A | 11/1995 | Reger |
| 5,476,589 A | 12/1995 | Bacino |
| 5,489,297 A | 2/1996 | Duran |
| 5,534,007 A | 7/1996 | St. Germain et al. |
| 5,549,663 A | 8/1996 | Cottone, Jr. |
| 5,554,183 A | 9/1996 | Nazari |
| 5,554,185 A | 9/1996 | Block et al. |
| 5,562,729 A | 10/1996 | Purdy |
| 5,628,791 A | 5/1997 | Bokros et al. |
| 5,673,102 A | 9/1997 | Suzuki et al. |
| 5,708,044 A | 1/1998 | Branca |
| 5,718,973 A | 2/1998 | Lewis et al. |
| 5,749,852 A | 5/1998 | Schwab et al. |
| 5,752,934 A | 5/1998 | Campbell et al. |
| 5,759,192 A | 6/1998 | Saunders |
| 5,769,884 A | 6/1998 | Solovay |
| 5,772,884 A | 6/1998 | Tanaka et al. |
| 5,788,626 A | 8/1998 | Thompson |
| 5,814,405 A | 9/1998 | Branca et al. |
| 5,824,043 A | 10/1998 | Cottone, Jr. |
| 5,843,158 A | 12/1998 | Lenker et al. |
| 5,843,161 A | 12/1998 | Solovay |
| 5,843,171 A | 12/1998 | Campbell et al. |
| 5,853,419 A | 12/1998 | Imran |
| 5,925,061 A | 7/1999 | Ogi et al. |
| 5,928,281 A | 7/1999 | Huynh et al. |
| 5,935,162 A | 8/1999 | Dang |
| 5,935,163 A | 8/1999 | Gabbay |
| 5,944,654 A | 8/1999 | Crawford |
| 5,957,974 A | 9/1999 | Thompson et al. |
| 6,010,529 A | 1/2000 | Herweck et al. |
| 6,013,854 A | 1/2000 | Moriuchi |
| 6,019,785 A | 2/2000 | Strecker |
| 6,042,588 A | 3/2000 | Munsinger et al. |
| 6,042,605 A | 3/2000 | Martin et al. |
| 6,042,606 A | 3/2000 | Frantzen |
| 6,086,612 A | 7/2000 | Jansen |
| 6,110,198 A | 8/2000 | Fogarty et al. |
| 6,117,169 A | 9/2000 | Moe |
| 6,129,758 A | 10/2000 | Love |
| 6,161,399 A | 12/2000 | Jayaraman |
| 6,165,211 A | 12/2000 | Thompson |
| 6,171,335 B1 | 1/2001 | Wheatley et al. |
| 6,174,329 B1 | 1/2001 | Callol et al. |
| 6,174,331 B1 | 1/2001 | Moe et al. |
| 6,190,406 B1 | 2/2001 | Duerig et al. |
| 6,197,143 B1 | 3/2001 | Bodnar |
| 6,217,609 B1 | 4/2001 | Haverkost |
| 6,245,012 B1 | 6/2001 | Kleshinski |
| 6,261,320 B1 | 7/2001 | Tam et al. |
| 6,261,620 B1 | 7/2001 | Leadbeater |
| 6,283,994 B1 | 9/2001 | Moe et al. |
| 6,283,995 B1 | 9/2001 | Moe et al. |
| 6,287,334 B1 | 9/2001 | Moll et al. |
| 6,328,763 B1 | 12/2001 | Love et al. |
| 6,334,873 B1 | 1/2002 | Lane et al. |
| 6,336,937 B1 | 1/2002 | Vonesh et al. |
| 6,352,552 B1 | 3/2002 | Levinson et al. |
| 6,379,382 B1 | 4/2002 | Yang |
| 6,436,132 B1 | 8/2002 | Patel et al. |
| 6,454,798 B1 | 9/2002 | Moe |
| 6,454,799 B1 | 9/2002 | Schreck |
| 6,461,382 B1 | 10/2002 | Cao |
| 6,461,665 B1 | 10/2002 | Scholander |
| 6,482,228 B1 | 11/2002 | Norred |
| 6,488,701 B1 | 12/2002 | Nolting et al. |
| 6,541,589 B1 | 4/2003 | Baillie |
| 6,558,418 B2 | 5/2003 | Carpentier et al. |
| 6,562,069 B2 | 5/2003 | Cai et al. |
| 6,582,464 B2 | 6/2003 | Gabbay |
| 6,613,086 B1 | 9/2003 | Moe et al. |
| 6,620,190 B1 | 9/2003 | Colone |
| 6,626,939 B1 | 9/2003 | Burnside et al. |
| 6,645,244 B2 | 11/2003 | Shu et al. |
| 6,666,885 B2 | 12/2003 | Moe |
| 6,673,102 B1 | 1/2004 | Vonesh et al. |
| 6,673,107 B1 | 1/2004 | Brandt et al. |
| 6,726,715 B2 | 4/2004 | Sutherland |
| 6,730,118 B2 | 5/2004 | Spenser et al. |
| 6,730,120 B2 | 5/2004 | Berg et al. |
| 6,755,856 B2 | 6/2004 | Fierens et al. |
| 6,755,857 B2 | 6/2004 | Peterson et al. |
| 6,758,858 B2 | 7/2004 | McCrea et al. |
| 6,890,350 B1 | 5/2005 | Walak |
| 6,893,460 B2 | 5/2005 | Spenser et al. |
| 6,916,338 B2 | 7/2005 | Speziali |
| 6,936,067 B2 | 8/2005 | Buchanan |
| 6,953,332 B1 | 10/2005 | Kurk et al. |
| 7,022,132 B2 | 4/2006 | Kocur |
| 7,049,380 B1 | 5/2006 | Chang et al. |
| 7,083,642 B2 | 8/2006 | Sirhan et al. |
| 7,105,018 B1 | 9/2006 | Yip et al. |
| 7,137,184 B2 | 11/2006 | Schreck |
| 7,163,556 B2 | 1/2007 | Xie et al. |
| 7,238,200 B2 | 7/2007 | Lee et al. |
| 7,247,167 B2 | 7/2007 | Gabbay |
| 7,306,729 B2 | 12/2007 | Bacino et al. |
| 7,381,218 B2 | 6/2008 | Schreck |
| 7,419,678 B2 | 9/2008 | Falotico |
| 7,462,675 B2 | 12/2008 | Chang et al. |
| 7,510,575 B2 | 3/2009 | Spenser et al. |
| 7,513,909 B2 | 4/2009 | Lane et al. |
| 7,531,611 B2 | 5/2009 | Sabol et al. |
| 7,563,277 B2 | 7/2009 | Case et al. |
| 7,708,775 B2 | 5/2010 | Rowe et al. |
| 7,727,274 B2 | 6/2010 | Zilla et al. |
| 7,758,640 B2 | 7/2010 | Vesely |
| 7,780,725 B2 | 8/2010 | Haug et al. |
| 7,789,908 B2 | 9/2010 | Sowinski et al. |
| 7,803,186 B1 | 9/2010 | Li et al. |
| 7,811,314 B2 | 10/2010 | Fierens et al. |
| 7,815,763 B2 | 10/2010 | Fierens et al. |
| 7,879,085 B2 | 2/2011 | Sowinski et al. |
| 7,887,562 B2 | 2/2011 | Young et al. |
| 7,914,569 B2 | 3/2011 | Nguyen et al. |
| 7,927,364 B2 | 4/2011 | Fierens et al. |
| 7,927,365 B2 | 4/2011 | Fierens et al. |
| 7,935,141 B2 | 5/2011 | Randall et al. |
| 7,967,829 B2 | 6/2011 | Gunderson et al. |
| 7,967,853 B2 | 6/2011 | Eidenschink et al. |
| 7,993,394 B2 | 8/2011 | Hariton et al. |
| 8,048,440 B2 | 11/2011 | Chang et al. |
| 8,062,359 B2 | 11/2011 | Marquez et al. |

(56) References Cited

U.S. PATENT DOCUMENTS

| | | |
|---|---|---|
| 8,092,523 B2 | 1/2012 | Li et al. |
| 8,167,935 B2 | 5/2012 | McGuckin et al. |
| 8,226,710 B2 | 7/2012 | Nguyen et al. |
| 8,246,678 B2 | 8/2012 | Salahieh et al. |
| 8,252,037 B2 | 8/2012 | Styrc et al. |
| 8,303,647 B2 | 11/2012 | Case |
| 8,349,000 B2 | 1/2013 | Schreck |
| 8,409,274 B2 | 4/2013 | Li et al. |
| 8,475,512 B2 | 7/2013 | Hunt |
| 8,545,525 B2 | 10/2013 | Surti et al. |
| 8,568,475 B2 | 10/2013 | Nguyen et al. |
| 8,585,753 B2 | 11/2013 | Scanlon et al. |
| 8,585,757 B2 | 11/2013 | Agathos |
| 8,628,566 B2 | 1/2014 | Eberhardt et al. |
| 8,637,144 B2 | 1/2014 | Ford |
| 8,709,077 B2 | 4/2014 | Schreck |
| 8,722,178 B2 | 5/2014 | Ashmead et al. |
| 8,728,103 B2 | 5/2014 | Surti et al. |
| 8,728,154 B2 | 5/2014 | Alkhatib |
| 8,784,481 B2 | 7/2014 | Alkhatib et al. |
| 8,801,774 B2 | 8/2014 | Silverman |
| 8,808,848 B2 | 8/2014 | Bacino |
| 8,845,709 B2 | 9/2014 | Styrc et al. |
| 8,845,721 B2 | 9/2014 | Braido et al. |
| 8,852,272 B2 | 10/2014 | Gross et al. |
| 8,870,948 B1 | 10/2014 | Erzberger et al. |
| 8,936,634 B2 | 1/2015 | Irwin et al. |
| 8,945,212 B2 | 2/2015 | Bruchman et al. |
| 8,961,599 B2 * | 2/2015 | Bruchman ............ A61F 2/2415 623/2.12 |
| 8,992,608 B2 | 3/2015 | Haug et al. |
| 9,039,757 B2 | 5/2015 | McLean et al. |
| 9,101,469 B2 | 8/2015 | Bruchman et al. |
| 9,107,771 B2 | 8/2015 | Wubbeling et al. |
| 9,125,740 B2 | 9/2015 | Morriss et al. |
| 9,139,669 B2 | 9/2015 | Xu et al. |
| 9,144,492 B2 | 9/2015 | Bruchman et al. |
| 9,168,131 B2 | 10/2015 | Yohanan et al. |
| 9,198,787 B2 | 12/2015 | Kratzberg et al. |
| 9,241,695 B2 | 1/2016 | Peavey et al. |
| 9,283,072 B2 | 3/2016 | Bruchman et al. |
| 9,295,552 B2 | 3/2016 | McLean et al. |
| 9,314,355 B2 | 4/2016 | Styrc et al. |
| 9,345,601 B2 | 5/2016 | Jantzen et al. |
| 9,375,308 B2 | 6/2016 | Norris |
| 9,393,110 B2 | 7/2016 | Levi et al. |
| 9,398,952 B2 | 7/2016 | Bruchman et al. |
| 9,399,085 B2 | 7/2016 | Cleek et al. |
| 9,504,565 B2 | 11/2016 | Armstrong |
| 9,554,786 B2 | 1/2017 | Carley et al. |
| 9,554,900 B2 | 1/2017 | Bruchman et al. |
| 9,597,181 B2 | 3/2017 | Christianson et al. |
| 9,629,718 B2 | 4/2017 | Gloss et al. |
| 9,681,948 B2 | 6/2017 | Levi et al. |
| 9,737,398 B2 | 8/2017 | Bruchman et al. |
| 9,737,422 B2 | 8/2017 | Armstrong et al. |
| 9,743,932 B2 | 8/2017 | Amplatz et al. |
| 9,795,496 B2 | 10/2017 | Armstrong et al. |
| 9,801,712 B2 | 10/2017 | Bruchman et al. |
| 9,827,089 B2 | 11/2017 | Bruchman et al. |
| 9,827,094 B2 | 11/2017 | Bennett |
| 9,839,540 B2 | 12/2017 | Armstrong et al. |
| 9,855,141 B2 | 1/2018 | Dienno et al. |
| 9,931,193 B2 | 4/2018 | Cully et al. |
| 9,931,204 B2 | 4/2018 | Rothstein et al. |
| 9,937,037 B2 | 4/2018 | Dienno et al. |
| 9,968,443 B2 | 5/2018 | Bruchman et al. |
| 10,039,638 B2 | 8/2018 | Bruchman et al. |
| 10,166,128 B2 | 1/2019 | Armstrong et al. |
| 10,279,084 B2 | 5/2019 | Goepfrich et al. |
| 10,285,808 B2 | 5/2019 | Bruchman et al. |
| 10,314,697 B2 | 6/2019 | Gassler |
| 10,321,986 B2 | 6/2019 | Bruchman et al. |
| 10,335,298 B2 | 7/2019 | Armstrong et al. |
| 10,342,659 B2 | 7/2019 | Bennett |
| 10,368,984 B2 | 8/2019 | Armstrong |
| 10,376,360 B2 | 8/2019 | Bruchman et al. |
| 10,441,416 B2 | 10/2019 | Oba et al. |
| 10,463,478 B2 | 11/2019 | Bruchman et al. |
| 10,507,124 B2 | 12/2019 | Armstrong et al. |
| 10,639,144 B2 | 5/2020 | Bruchman et al. |
| 10,660,745 B2 | 5/2020 | Bruchman et al. |
| 10,881,507 B2 | 1/2021 | Bruchman et al. |
| 10,980,633 B2 | 4/2021 | Dienno et al. |
| 11,020,221 B2 | 6/2021 | Arcaro et al. |
| 11,039,917 B2 | 6/2021 | Bruchman et al. |
| D926,322 S | 7/2021 | Bennett et al. |
| 11,065,112 B2 | 7/2021 | Gassler |
| 11,090,153 B2 | 8/2021 | Haarer et al. |
| 11,109,963 B2 | 9/2021 | Dienno et al. |
| 11,123,183 B2 | 9/2021 | Bennett et al. |
| 2001/0053929 A1 | 12/2001 | Vonesh et al. |
| 2002/0045936 A1 | 4/2002 | Moe |
| 2002/0055773 A1 | 5/2002 | Campbell et al. |
| 2002/0076542 A1 | 6/2002 | Kramer et al. |
| 2002/0082687 A1 | 6/2002 | Moe |
| 2002/0133226 A1 | 9/2002 | Marquez et al. |
| 2002/0183840 A1 | 12/2002 | Lapeyre et al. |
| 2002/0198588 A1 | 12/2002 | Armstrong et al. |
| 2002/0198594 A1 | 12/2002 | Schreck |
| 2003/0014105 A1 | 1/2003 | Cao |
| 2003/0027332 A1 | 2/2003 | Lafrance et al. |
| 2003/0055494 A1 | 3/2003 | Bezuidenhout et al. |
| 2003/0055496 A1 | 3/2003 | Cai et al. |
| 2003/0060871 A1 | 3/2003 | Hill et al. |
| 2003/0074052 A1 | 4/2003 | Besselink et al. |
| 2003/0097175 A1 | 5/2003 | O'Connor et al. |
| 2003/0114913 A1 | 6/2003 | Spenser et al. |
| 2003/0180488 A1 | 9/2003 | Lim et al. |
| 2003/0229394 A1 | 12/2003 | Ogle et al. |
| 2004/0024442 A1 | 2/2004 | Sowinski et al. |
| 2004/0024448 A1 | 2/2004 | Chang et al. |
| 2004/0024451 A1 | 2/2004 | Johnson et al. |
| 2004/0026245 A1 | 2/2004 | Agarwal et al. |
| 2004/0039436 A1 | 2/2004 | Spenser et al. |
| 2004/0044400 A1 | 3/2004 | Cheng et al. |
| 2004/0044401 A1 | 3/2004 | Bales et al. |
| 2004/0133266 A1 | 7/2004 | Clerc et al. |
| 2004/0170782 A1 | 9/2004 | Wang et al. |
| 2004/0176839 A1 | 9/2004 | Huynh et al. |
| 2004/0224442 A1 | 11/2004 | Grigg |
| 2004/0243222 A1 | 12/2004 | Osborne et al. |
| 2004/0260277 A1 | 12/2004 | Maguire |
| 2004/0260393 A1 | 12/2004 | Rahdert et al. |
| 2005/0027348 A1 | 2/2005 | Case et al. |
| 2005/0080476 A1 | 4/2005 | Gunderson et al. |
| 2005/0119722 A1 | 6/2005 | Styrc et al. |
| 2005/0137680 A1 | 6/2005 | Ortiz et al. |
| 2005/0137682 A1 | 6/2005 | Justino |
| 2005/0261765 A1 | 11/2005 | Liddicoat |
| 2005/0283224 A1 | 12/2005 | King |
| 2006/0008497 A1 | 1/2006 | Gabbay |
| 2006/0009835 A1 | 1/2006 | Osborne et al. |
| 2006/0015171 A1 | 1/2006 | Armstrong |
| 2006/0036311 A1 | 2/2006 | Nakayama et al. |
| 2006/0041091 A1 | 2/2006 | Chang et al. |
| 2006/0106337 A1 | 5/2006 | Blankenship |
| 2006/0118236 A1 | 6/2006 | House et al. |
| 2006/0122693 A1 | 6/2006 | Biadillah et al. |
| 2006/0135985 A1 | 6/2006 | Cox et al. |
| 2006/0154365 A1 | 7/2006 | Ratcliffe et al. |
| 2006/0161241 A1 | 7/2006 | Barbut et al. |
| 2006/0190070 A1 | 8/2006 | Dieck et al. |
| 2006/0229718 A1 | 10/2006 | Marquez |
| 2006/0229719 A1 | 10/2006 | Marquez et al. |
| 2006/0259133 A1 | 11/2006 | Sowinski et al. |
| 2006/0259136 A1 | 11/2006 | Nguyen et al. |
| 2006/0265053 A1 | 11/2006 | Hunt |
| 2006/0271091 A1 | 11/2006 | Campbell et al. |
| 2006/0276813 A1 | 12/2006 | Greenberg |
| 2006/0276883 A1 | 12/2006 | Greenberg et al. |
| 2006/0276888 A1 | 12/2006 | Lee et al. |
| 2006/0282162 A1 | 12/2006 | Nguyen et al. |
| 2006/0290027 A1 | 12/2006 | O'Connor et al. |

(56) References Cited

U.S. PATENT DOCUMENTS

| | | |
|---|---|---|
| 2007/0010876 A1 | 1/2007 | Salahieh et al. |
| 2007/0012624 A1 | 1/2007 | Bacino et al. |
| 2007/0021826 A1 | 1/2007 | Case et al. |
| 2007/0060999 A1 | 3/2007 | Randall et al. |
| 2007/0118210 A1 | 5/2007 | Pinchuk |
| 2007/0129786 A1 | 6/2007 | Beach et al. |
| 2007/0207186 A1* | 9/2007 | Scanlon ............... A61F 2/91 623/1.42 |
| 2007/0207816 A1 | 9/2007 | Spain, Jr. |
| 2007/0208421 A1 | 9/2007 | Quigley |
| 2007/0213800 A1 | 9/2007 | Fierens et al. |
| 2007/0244552 A1 | 10/2007 | Salahieh et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2008/0009940 A1 | 1/2008 | Cribier |
| 2008/0026190 A1 | 1/2008 | King et al. |
| 2008/0039934 A1 | 2/2008 | Styrc |
| 2008/0051876 A1 | 2/2008 | Ta et al. |
| 2008/0065198 A1 | 3/2008 | Quintessenza |
| 2008/0071369 A1 | 3/2008 | Tuval et al. |
| 2008/0082154 A1 | 4/2008 | Tseng et al. |
| 2008/0086202 A1* | 4/2008 | Lapeyre ............... A61F 2/2403 623/2.33 |
| 2008/0097301 A1 | 4/2008 | Alpini et al. |
| 2008/0097401 A1 | 4/2008 | Trapp et al. |
| 2008/0097579 A1 | 4/2008 | Shanley et al. |
| 2008/0097582 A1 | 4/2008 | Shanley et al. |
| 2008/0119943 A1 | 5/2008 | Armstrong et al. |
| 2008/0133004 A1 | 6/2008 | White |
| 2008/0140178 A1 | 6/2008 | Rasmussen et al. |
| 2008/0195199 A1 | 8/2008 | Kheradvar et al. |
| 2008/0208327 A1 | 8/2008 | Rowe |
| 2008/0220041 A1 | 9/2008 | Brito et al. |
| 2008/0228263 A1 | 9/2008 | Ryan |
| 2008/0300678 A1 | 12/2008 | Eidenschink et al. |
| 2008/0319531 A1 | 12/2008 | Doran et al. |
| 2009/0005854 A1 | 1/2009 | Huang et al. |
| 2009/0030499 A1 | 1/2009 | Bebb et al. |
| 2009/0036976 A1 | 2/2009 | Beach et al. |
| 2009/0043373 A1 | 2/2009 | Arnault et al. |
| 2009/0104247 A1 | 4/2009 | Pacetti |
| 2009/0112309 A1* | 4/2009 | Jaramillo ............... A61F 2/2415 623/1.26 |
| 2009/0117334 A1 | 5/2009 | Sogard et al. |
| 2009/0138079 A1 | 5/2009 | Tuval et al. |
| 2009/0157175 A1 | 6/2009 | Benichou |
| 2009/0182413 A1 | 7/2009 | Burkart et al. |
| 2009/0240320 A1 | 9/2009 | Tuval et al. |
| 2009/0264997 A1 | 10/2009 | Salahieh et al. |
| 2009/0276039 A1 | 11/2009 | Meretei |
| 2009/0287305 A1 | 11/2009 | Amalaha |
| 2009/0292350 A1 | 11/2009 | Eberhardt et al. |
| 2009/0306762 A1 | 12/2009 | McCullagh et al. |
| 2009/0306766 A1 | 12/2009 | McDermott et al. |
| 2010/0016940 A1 | 1/2010 | Shokoohi et al. |
| 2010/0023114 A1 | 1/2010 | Chambers et al. |
| 2010/0036021 A1 | 2/2010 | Lee et al. |
| 2010/0036484 A1 | 2/2010 | Hariton et al. |
| 2010/0049294 A1 | 2/2010 | Zukowski et al. |
| 2010/0082094 A1 | 4/2010 | Quadri et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0131056 A1 | 5/2010 | Lapeyre |
| 2010/0137998 A1 | 6/2010 | Sobrino-Serrano et al. |
| 2010/0145438 A1 | 6/2010 | Barone |
| 2010/0159171 A1 | 6/2010 | Clough |
| 2010/0168839 A1 | 7/2010 | Braido et al. |
| 2010/0185274 A1 | 7/2010 | Moaddeb et al. |
| 2010/0185277 A1 | 7/2010 | Braido et al. |
| 2010/0191320 A1 | 7/2010 | Straubinger et al. |
| 2010/0204781 A1 | 8/2010 | Alkhatib |
| 2010/0204785 A1 | 8/2010 | Alkhatib |
| 2010/0211165 A1 | 8/2010 | Schreck |
| 2010/0217382 A1 | 8/2010 | Chau et al. |
| 2010/0248324 A1 | 9/2010 | Xu et al. |
| 2010/0249923 A1 | 9/2010 | Alkhatib et al. |
| 2010/0256738 A1 | 10/2010 | Berglund |
| 2010/0262231 A1 | 10/2010 | Tuval et al. |
| 2010/0286760 A1 | 11/2010 | Beach et al. |
| 2010/0298931 A1 | 11/2010 | Quadri et al. |
| 2010/0305682 A1 | 12/2010 | Furst |
| 2011/0009953 A1 | 1/2011 | Luk et al. |
| 2011/0040366 A1 | 2/2011 | Goetz et al. |
| 2011/0054515 A1 | 3/2011 | Bridgeman et al. |
| 2011/0064781 A1 | 3/2011 | Cleek et al. |
| 2011/0087318 A1 | 4/2011 | Daugherty et al. |
| 2011/0160836 A1 | 6/2011 | Behan |
| 2011/0172784 A1 | 7/2011 | Richter et al. |
| 2011/0208283 A1 | 8/2011 | Rust |
| 2011/0218619 A1 | 9/2011 | Benichou et al. |
| 2011/0251678 A1 | 10/2011 | Eidenschink et al. |
| 2011/0257739 A1 | 10/2011 | Corbett |
| 2011/0282439 A1 | 11/2011 | Thill et al. |
| 2011/0295363 A1 | 12/2011 | Girard et al. |
| 2012/0035722 A1 | 2/2012 | Tuval |
| 2012/0078357 A1 | 3/2012 | Conklin |
| 2012/0083839 A1 | 4/2012 | Letac et al. |
| 2012/0089223 A1 | 4/2012 | Nguyen et al. |
| 2012/0101567 A1 | 4/2012 | Jansen |
| 2012/0101571 A1 | 4/2012 | Thambar et al. |
| 2012/0116496 A1 | 5/2012 | Chuter et al. |
| 2012/0116498 A1 | 5/2012 | Chuter et al. |
| 2012/0123529 A1 | 5/2012 | Levi et al. |
| 2012/0123530 A1 | 5/2012 | Carpentier et al. |
| 2012/0130468 A1 | 5/2012 | Khosravi et al. |
| 2012/0130471 A1 | 5/2012 | Shoemaker et al. |
| 2012/0185038 A1 | 7/2012 | Fish et al. |
| 2012/0253453 A1 | 10/2012 | Bruchman et al. |
| 2012/0290082 A1 | 11/2012 | Quint et al. |
| 2012/0323211 A1 | 12/2012 | Ogle et al. |
| 2012/0323315 A1* | 12/2012 | Bruchman ............ A61F 2/2415 623/2.12 |
| 2013/0018456 A1 | 1/2013 | Li et al. |
| 2013/0018458 A1 | 1/2013 | Yohanan et al. |
| 2013/0079700 A1 | 3/2013 | Ballard et al. |
| 2013/0110229 A1* | 5/2013 | Bokeriya ............... A61F 2/2409 623/2.19 |
| 2013/0116655 A1 | 5/2013 | Bacino et al. |
| 2013/0131780 A1* | 5/2013 | Armstrong ............... A61F 2/88 623/1.13 |
| 2013/0150956 A1 | 6/2013 | Yohanan et al. |
| 2013/0158647 A1 | 6/2013 | Norris et al. |
| 2013/0166021 A1 | 6/2013 | Bruchman et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0204347 A1 | 8/2013 | Armstrong et al. |
| 2013/0204360 A1 | 8/2013 | Gainor |
| 2013/0253466 A1 | 9/2013 | Campbell et al. |
| 2013/0297003 A1 | 11/2013 | Pinchuk |
| 2013/0338755 A1 | 12/2013 | Goetz et al. |
| 2014/0005771 A1 | 1/2014 | Braido et al. |
| 2014/0005773 A1 | 1/2014 | Wheatley |
| 2014/0031924 A1 | 1/2014 | Bruchman et al. |
| 2014/0031927 A1 | 1/2014 | Bruchman et al. |
| 2014/0094898 A1 | 4/2014 | Borck |
| 2014/0106951 A1 | 4/2014 | Brandon |
| 2014/0135897 A1 | 5/2014 | Cully et al. |
| 2014/0135908 A1* | 5/2014 | Glozman ............ A61F 2/2412 623/2.11 |
| 2014/0163671 A1 | 6/2014 | Bruchman et al. |
| 2014/0163673 A1 | 6/2014 | Bruchman et al. |
| 2014/0172066 A1 | 6/2014 | Goepfrich et al. |
| 2014/0172069 A1 | 6/2014 | Roeder et al. |
| 2014/0172077 A1 | 6/2014 | Bruchman et al. |
| 2014/0172078 A1 | 6/2014 | Bruchman et al. |
| 2014/0172079 A1 | 6/2014 | Bruchman et al. |
| 2014/0172082 A1 | 6/2014 | Bruchman et al. |
| 2014/0172083 A1 | 6/2014 | Bruchman et al. |
| 2014/0180400 A1 | 6/2014 | Bruchman et al. |
| 2014/0180402 A1 | 6/2014 | Bruchman et al. |
| 2014/0194968 A1 | 7/2014 | Zukowski |

(56) References Cited

U.S. PATENT DOCUMENTS

| | | |
|---|---|---|
| 2014/0222140 A1 | 8/2014 | Schreck |
| 2014/0236289 A1 | 8/2014 | Alkhatib |
| 2014/0277413 A1 | 9/2014 | Arnold et al. |
| 2014/0277418 A1 | 9/2014 | Miller |
| 2014/0296969 A1 | 10/2014 | Tegels et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0343670 A1 | 11/2014 | Bakis et al. |
| 2015/0005870 A1 | 1/2015 | Kovach et al. |
| 2015/0018944 A1 | 1/2015 | O'Connell et al. |
| 2015/0088250 A1 | 3/2015 | Zeng et al. |
| 2015/0105856 A1 | 4/2015 | Rowe et al. |
| 2015/0142100 A1 | 5/2015 | Morriss et al. |
| 2015/0157456 A1 | 6/2015 | Armstrong |
| 2015/0157770 A1 | 6/2015 | Cully et al. |
| 2015/0224231 A1 | 8/2015 | Bruchman et al. |
| 2015/0245910 A1 | 9/2015 | Righini et al. |
| 2015/0313871 A1 | 11/2015 | Li et al. |
| 2015/0366663 A1 | 12/2015 | Bruchman et al. |
| 2015/0366664 A1 | 12/2015 | Guttenberg et al. |
| 2016/0001469 A1 | 1/2016 | Bacchereti et al. |
| 2016/0015422 A1 | 1/2016 | De et al. |
| 2016/0074161 A1 | 3/2016 | Bennett |
| 2016/0113699 A1 | 4/2016 | Sverdlik et al. |
| 2016/0157998 A1 | 6/2016 | Bruchman et al. |
| 2016/0175095 A1 | 6/2016 | Dienno et al. |
| 2016/0175096 A1 | 6/2016 | Dienno et al. |
| 2016/0206424 A1 | 7/2016 | Al-Jilaihawi et al. |
| 2016/0213465 A1 | 7/2016 | Girard et al. |
| 2016/0235525 A1 | 8/2016 | Rothstein et al. |
| 2016/0310268 A1 | 10/2016 | Oba et al. |
| 2016/0317299 A1 | 11/2016 | Alkhatib |
| 2017/0027727 A1 | 2/2017 | Wuebbeling et al. |
| 2017/0042674 A1 | 2/2017 | Armstrong |
| 2017/0056169 A1 | 3/2017 | Johnson et al. |
| 2017/0065400 A1 | 3/2017 | Armstrong et al. |
| 2017/0095330 A1 | 4/2017 | Malewicz et al. |
| 2017/0095331 A1 | 4/2017 | Spenser et al. |
| 2017/0100236 A1 | 4/2017 | Robertson et al. |
| 2017/0105854 A1 | 4/2017 | Treacy et al. |
| 2017/0106176 A1 | 4/2017 | Taft et al. |
| 2017/0128199 A1 | 5/2017 | Gurovich et al. |
| 2017/0156859 A1 | 6/2017 | Chang et al. |
| 2017/0165066 A1 | 6/2017 | Rothstein |
| 2017/0165067 A1 | 6/2017 | Barajas-Torres et al. |
| 2017/0216062 A1 | 8/2017 | Armstrong et al. |
| 2017/0224481 A1 | 8/2017 | Spenser et al. |
| 2017/0252153 A1 | 9/2017 | Chau et al. |
| 2017/0348101 A1 | 12/2017 | Vaughn et al. |
| 2018/0021128 A1 | 1/2018 | Bruchman et al. |
| 2018/0021129 A1 | 1/2018 | Peterson et al. |
| 2018/0125646 A1 | 5/2018 | Bruchman et al. |
| 2018/0177583 A1 | 6/2018 | Cully et al. |
| 2018/0221144 A1 | 8/2018 | Bruchman et al. |
| 2018/0318070 A1 | 11/2018 | Bruchman et al. |
| 2019/0076245 A1 | 3/2019 | Arcaro et al. |
| 2019/0091014 A1 | 3/2019 | Arcaro et al. |
| 2019/0091015 A1 | 3/2019 | Dienno et al. |
| 2019/0110893 A1 | 4/2019 | Haarer et al. |
| 2019/0125517 A1 | 5/2019 | Cully et al. |
| 2019/0125528 A1 | 5/2019 | Busalacchi et al. |
| 2019/0125530 A1 | 5/2019 | Arcaro et al. |
| 2019/0125531 A1 | 5/2019 | Bennett et al. |
| 2019/0125534 A1 | 5/2019 | Arcaro et al. |
| 2019/0209292 A1 | 7/2019 | Bruchman et al. |
| 2019/0209739 A1 | 7/2019 | Goepfrich et al. |
| 2019/0216592 A1 | 7/2019 | Cully et al. |
| 2019/0247185 A1 | 8/2019 | Gassler |
| 2019/0254815 A1 | 8/2019 | Bruchman et al. |
| 2019/0269505 A1 | 9/2019 | Bruchman et al. |
| 2019/0314154 A1 | 10/2019 | Armstrong |
| 2019/0328525 A1 | 10/2019 | Noe et al. |
| 2019/0374339 A1 | 12/2019 | Bennett |
| 2020/0000578 A1 | 1/2020 | Bruchman et al. |
| 2020/0022828 A1 | 1/2020 | Armstrong et al. |
| 2020/0179663 A1 | 6/2020 | McDaniel et al. |
| 2020/0237497 A1 | 7/2020 | Silverman et al. |
| 2020/0237505 A1 | 7/2020 | Bruchman et al. |
| 2020/0246137 A1 | 8/2020 | Bruchman et al. |
| 2020/0276014 A1 | 9/2020 | Burkart et al. |
| 2021/0121289 A1 | 4/2021 | Bruchman et al. |
| 2021/0177589 A1 | 6/2021 | Arcaro et al. |
| 2021/0307905 A1 | 10/2021 | Arcaro et al. |
| 2021/0338422 A1 | 11/2021 | Dienno et al. |
| 2021/0346156 A1 | 11/2021 | Haarer et al. |
| 2021/0361420 A1 | 11/2021 | Bennett et al. |
| 2021/0393399 A1 | 12/2021 | Arcaro et al. |
| 2022/0000611 A1 | 1/2022 | Arcaro et al. |
| 2022/0023032 A1 | 1/2022 | Bruchman et al. |

FOREIGN PATENT DOCUMENTS

| | | |
|---|---|---|
| CA | 2462509 A1 | 4/2003 |
| CA | 2849030 A1 | 4/2013 |
| CA | 2878691 A1 | 1/2014 |
| CA | 2964546 A1 | 1/2014 |
| CA | 2960034 A1 | 3/2016 |
| CN | 101057796 A | 10/2007 |
| CN | 101091675 A | 12/2007 |
| CN | 101188985 A | 5/2008 |
| CN | 101374477 A | 2/2009 |
| CN | 101420913 A | 4/2009 |
| CN | 101849863 A | 10/2010 |
| CN | 101902989 A | 12/2010 |
| CN | 101926699 A | 12/2010 |
| CN | 201744060 U | 2/2011 |
| CN | 102015009 A | 4/2011 |
| CN | 102119013 A | 7/2011 |
| CN | 102292053 A | 12/2011 |
| CN | 102438546 A | 5/2012 |
| CN | 102573703 A | 7/2012 |
| CN | 102652694 A | 9/2012 |
| CN | 102764169 A | 11/2012 |
| CN | 102791223 A | 11/2012 |
| CN | 102883684 A | 1/2013 |
| CN | 103079498 A | 5/2013 |
| CN | 103228232 A | 7/2013 |
| CN | 103237524 A | 8/2013 |
| CN | 103384505 A | 11/2013 |
| CN | 103732183 A | 4/2014 |
| CN | 103781439 A | 5/2014 |
| CN | 103945796 A | 7/2014 |
| CN | 104114127 A | 10/2014 |
| CN | 104487023 A | 4/2015 |
| CN | 104507417 A | 4/2015 |
| CN | 105007955 A | 10/2015 |
| CN | 105101911 A | 11/2015 |
| CN | 105263445 A | 1/2016 |
| CN | 105792780 A | 7/2016 |
| CN | 106668949 A | 5/2017 |
| CN | 106714733 A | 5/2017 |
| CN | 106794065 A | 5/2017 |
| CN | 107106294 A | 8/2017 |
| CN | 107690323 A | 2/2018 |
| DE | 212013000104 U1 | 11/2014 |
| EP | 0293090 A2 | 11/1988 |
| EP | 0313263 A2 | 4/1989 |
| EP | 0582870 A2 | 2/1994 |
| EP | 0775472 A2 | 5/1997 |
| EP | 0815806 A2 | 1/1998 |
| EP | 0893108 A2 | 1/1999 |
| EP | 1318775 A1 | 6/2003 |
| EP | 1666003 A1 | 6/2006 |
| EP | 1395205 B1 | 7/2008 |
| EP | 1235537 B1 | 12/2008 |
| EP | 2193762 A1 | 6/2010 |
| EP | 2255750 A2 | 12/2010 |
| EP | 2400923 A1 | 1/2012 |
| EP | 2359774 B1 | 1/2013 |
| EP | 2591100 A2 | 5/2013 |
| EP | 2109417 B1 | 11/2013 |
| EP | 3142608 A1 | 3/2017 |
| EP | 3797738 A1 | 3/2021 |

(56) References Cited

FOREIGN PATENT DOCUMENTS

| | | |
|---|---|---|
| FR | 2591100 A1 | 6/1987 |
| GB | 2312485 A | 10/1997 |
| GB | 2513194 A | 10/2014 |
| JP | 44-032400 | 12/1969 |
| JP | 1969-032400 B | 12/1969 |
| JP | 02-000645 A | 1/1990 |
| JP | 09-241412 A | 9/1997 |
| JP | 10-507097 A | 7/1998 |
| JP | 11-290448 A | 10/1999 |
| JP | 11-512635 A | 11/1999 |
| JP | 2000-511459 A | 9/2000 |
| JP | 2000-513248 A | 10/2000 |
| JP | 2001-508641 A | 7/2001 |
| JP | 2001-508681 A | 7/2001 |
| JP | 2001-509702 A | 7/2001 |
| JP | 2001-511030 A | 8/2001 |
| JP | 2002-525169 A | 8/2002 |
| JP | 2002-541915 A | 12/2002 |
| JP | 2004-510471 A | 4/2004 |
| JP | 2005-500101 A | 1/2005 |
| JP | 2005-512611 A | 5/2005 |
| JP | 2007-526098 A | 9/2007 |
| JP | 2007-536989 A | 12/2007 |
| JP | 2008-506459 A | 3/2008 |
| JP | 2008-535572 A | 9/2008 |
| JP | 4335487 B2 | 9/2009 |
| JP | 2010-500107 A | 1/2010 |
| JP | 2010-504174 A | 2/2010 |
| JP | 2010-517623 A | 5/2010 |
| JP | 2010-528761 A | 8/2010 |
| JP | 2010-188189 A | 9/2010 |
| JP | 2010-535075 A | 11/2010 |
| JP | 2010-536527 A | 12/2010 |
| JP | 2012-504031 A | 2/2012 |
| JP | 2012-152563 A | 8/2012 |
| JP | 2013-543399 A | 12/2013 |
| JP | 2014-513585 A | 6/2014 |
| JP | 2014-517720 A | 7/2014 |
| JP | 2016-501104 A | 1/2016 |
| JP | 2016-518948 A | 6/2016 |
| JP | 2017-527397 A | 9/2017 |
| JP | 2018-079352 A | 5/2018 |
| JP | 6392778 B2 | 9/2018 |
| JP | 6802300 B2 | 12/2020 |
| RU | 2124986 C1 | 1/1999 |
| RU | 2434604 C1 | 11/2011 |
| WO | 94/13224 A1 | 6/1994 |
| WO | 94/16802 A1 | 8/1994 |
| WO | 95/05555 A1 | 2/1995 |
| WO | 95/09586 A1 | 4/1995 |
| WO | 96/02212 A1 | 2/1996 |
| WO | 96/07370 A1 | 3/1996 |
| WO | 96/40348 A1 | 12/1996 |
| WO | 97/10871 A1 | 3/1997 |
| WO | 99/26558 A1 | 6/1999 |
| WO | 00/18333 A1 | 4/2000 |
| WO | 00/41649 A1 | 7/2000 |
| WO | 00/47271 A1 | 8/2000 |
| WO | 00/62716 A1 | 10/2000 |
| WO | 01/28453 A2 | 4/2001 |
| WO | 01/41679 A1 | 6/2001 |
| WO | 01/64278 A1 | 9/2001 |
| WO | 01/74272 A2 | 10/2001 |
| WO | 02/07795 A2 | 1/2002 |
| WO | 02/24118 A1 | 3/2002 |
| WO | 02/24119 A1 | 3/2002 |
| WO | 02/45933 A2 | 6/2002 |
| WO | 02/47468 A1 | 6/2002 |
| WO | 02/60506 A1 | 8/2002 |
| WO | 2002/100301 A1 | 12/2002 |
| WO | 03/03946 A1 | 1/2003 |
| WO | 03/07795 A2 | 1/2003 |
| WO | 03/47468 A1 | 6/2003 |
| WO | 03/90834 A2 | 11/2003 |
| WO | 2004/000375 A1 | 12/2003 |
| WO | 2005/112827 A2 | 12/2005 |
| WO | 2006/019626 A2 | 2/2006 |
| WO | 2006/058322 A2 | 6/2006 |
| WO | 2006/108090 A2 | 10/2006 |
| WO | 2007/016251 A2 | 2/2007 |
| WO | 2008/021002 A1 | 2/2008 |
| WO | 2008/028964 A2 | 3/2008 |
| WO | 2008/036870 A2 | 3/2008 |
| WO | 2008/049045 A2 | 4/2008 |
| WO | 2008/052421 A1 | 5/2008 |
| WO | 2008/091589 A1 | 7/2008 |
| WO | 2008/021006 A3 | 8/2008 |
| WO | 2008/097589 A1 | 8/2008 |
| WO | 2008/097592 A2 | 8/2008 |
| WO | 2008/150529 A1 | 12/2008 |
| WO | 2009/017827 A1 | 2/2009 |
| WO | 2009/029199 A1 | 3/2009 |
| WO | 2009/045332 A2 | 4/2009 |
| WO | 2009/100210 A1 | 8/2009 |
| WO | 2009/108355 A1 | 9/2009 |
| WO | 2010/006783 A1 | 1/2010 |
| WO | 2010/008570 A1 | 1/2010 |
| WO | 2010/030766 A1 | 3/2010 |
| WO | 2010/037141 A1 | 4/2010 |
| WO | 2010/057262 A1 | 5/2010 |
| WO | 2010/086460 A1 | 8/2010 |
| WO | 2010/132707 A1 | 11/2010 |
| WO | 2010/150208 A2 | 12/2010 |
| WO | 2011/098565 A1 | 8/2011 |
| WO | 2011/109450 A2 | 9/2011 |
| WO | 2011/109801 A2 | 9/2011 |
| WO | 2011/112706 A2 | 9/2011 |
| WO | 2012/004460 A2 | 1/2012 |
| WO | 2012/011261 A1 | 1/2012 |
| WO | 2012/040643 A2 | 3/2012 |
| WO | 2012/047644 A2 | 4/2012 |
| WO | 2012/065080 A2 | 5/2012 |
| WO | 2012/082952 A2 | 6/2012 |
| WO | 2012/099979 A1 | 7/2012 |
| WO | 2012/110767 A2 | 8/2012 |
| WO | 2012/116368 A2 | 8/2012 |
| WO | 2012/135603 A2 | 10/2012 |
| WO | 2012/158944 A1 | 11/2012 |
| WO | 2012/167131 A1 | 12/2012 |
| WO | 2013/074663 A2 | 5/2013 |
| WO | 2013/074990 A1 | 5/2013 |
| WO | 2013/096854 A2 | 6/2013 |
| WO | 2013/109337 A1 | 7/2013 |
| WO | 2014/018189 A2 | 1/2014 |
| WO | 2014/018432 A2 | 1/2014 |
| WO | 2014/099150 | 6/2014 |
| WO | 2014/099163 A1 | 6/2014 |
| WO | 2014/099722 A1 | 6/2014 |
| WO | 2014/144937 A2 | 9/2014 |
| WO | 2015/045002 A1 | 4/2015 |
| WO | 2015/085138 A1 | 6/2015 |
| WO | 2015/171743 A2 | 11/2015 |
| WO | 2015/173794 A1 | 11/2015 |
| WO | 2016/028591 A1 | 2/2016 |
| WO | 2016/044223 A1 | 3/2016 |
| WO | 2016/100913 A1 | 6/2016 |
| WO | 2016/172349 A1 | 10/2016 |
| WO | 2016/186909 A1 | 11/2016 |
| WO | 2017/038145 A1 | 3/2017 |
| WO | 2017/096157 A1 | 6/2017 |
| WO | 2019/067219 A1 | 4/2019 |
| WO | 2019/067220 A1 | 4/2019 |
| WO | 2019/074607 A1 | 4/2019 |
| WO | 2019/074869 A1 | 4/2019 |
| WO | 2019/089138 A1 | 5/2019 |

OTHER PUBLICATIONS

EPO Form 1002 for EP16196687.4 Filed Dec. 28, 2016.
Google Image Search Results, "S-Shaped", accessed Nov. 1, 2013.
Nakayama, Yasuhide. Microporous Stent Achieves Brain Aneurysm Occlusion Without Disturbing Branching Flow. NeuroNews Nov. 2012; 8:1-2.

(56) References Cited

OTHER PUBLICATIONS

Nishi S, Nakayama Y, Ishibashi-Ueda FI, Okamoto Y, Yoshida M. Development of microporous self-expanding stent grafts for treating cerebral aneurysms: designing micropores to control intimal hyperplasia. J Artif Organs 2011; 14:348-356.
Priority Document for U.S. Appl. No. 61/739,721, received by the International Bureau Jan. 3, 2014, 1 page.
Application Data sheet, Drawings, Specification, Claims, and Abstract filed under U.S. Appl. No. 13/843,196 on Mar. 15, 2013, 52 pages.
Clough, Norman E. Introducing a New Family of GORE ePTFE Fibers (2007), pp. 1-10.
English translation of RU2434604 (C1), filed Apr. 30, 2010, translation powered by EPO and Google, 8 pages.
International Search Report and Written Opinion received for PCT Patent Application No. PCT/US13/68390, mailed on Apr. 29, 2014, 16 pages.
Mano Thubrikar, "The Aortic Valve", Chapter 1: Geometry of the Aortic Valve, CRC Press, Inc., Informa Healthcare, 2011, 40 pages.
Norman E. Clough. Introducing a New Family of GORE (Trademark) ePTFE Fibers (2007).
Opposition from EP16196687.4, mailed on Dec. 12, 2019, 38 pages.
Opposition from EP17187595.8, filed Sep. 12, 2019, 50 pages.

\* cited by examiner

GEOMETRIC CONTROL OF BENDING CHARACTER IN PROSTHETIC HEART VALVE LEAFLETS

CROSS-REFERENCE TO RELATED APPLICATIONS

This application is a continuation of U.S. application Ser. No. 13/835,988, filed Mar. 15, 2013, which claims priority to provisional application Ser. No. 61/739,721 filed Dec. 19, 2012, which are herein incorporated by reference in their entireties.

FIELD

The present disclosure relates generally to prosthetic valves, and more specifically, synthetic flexible leaflet-type prosthetic valve devices, systems, and methods.

BACKGROUND

Bioprosthetic valves have been developed that attempt to mimic the function and performance of a native valve. Flexible leaflets are fabricated from biological tissue such as bovine pericardium. In some valve designs the biological tissue is sewn onto a relatively rigid frame that supports the leaflets and provides dimensional stability when implanted. Although bioprosthetic valves can provide excellent hemodynamic and biomechanical performance in the short term, they are prone to calcification and cusp tears, among other failure modes, requiring reoperation and replacement.

Bioprosthetic valves have been developed that attempt to mimic the function and performance of a native valve. Flexible leaflets are fabricated from biological tissue such as bovine pericardium. In some valve designs the biological tissue is sewn onto a relatively rigid frame that supports the leaflets and provides dimensional stability when implanted. Although bioprosthetic valves can provide excellent hemodynamic and biomechanical performance in the short term, they are prone to calcification and cusp tears, among other failure modes, requiring reoperation and replacement.

Attempts have been made to use synthetic materials, such as polyurethane, among others, as a substitute for the biological tissue, to provide a more durable flexible leaflet prosthetic valve, herein referred to as a synthetic leaflet valve (SLV). However, synthetic leaflet valves have not become a valid valve replacement option since they suffer premature failure, due to, among other things, suboptimal design and lack of a durable synthetic material.

The leaflet moves under the influence of fluid pressure. In operation, the leaflets open when the upstream fluid pressure exceeds the downstream fluid pressure and close when the downstream fluid pressure exceeds the upstream fluid pressure. The free edges of the leaflets coapt under the influence of downstream fluid pressure closing the valve to prevent downstream blood from flowing retrograde through the valve.

Valve durability under the repetitive loads of the leaflets opening and closing is dependent, in part, on the load distribution between the leaflet and the frame. Further, substantial load is encountered on the leaflet when in the closed position. Mechanical failure of the leaflet can arise, for example, at the mounting edge, where the flexible leaflet is supported by the relatively rigid frame. The repetitive loads of leaflet opening and closing leads to material failure by fatigue, creep or other mechanism, depending in part on the leaflet material. Mechanical failure at the mounting edge is especially prevalent with synthetic leaflets.

The durability of the valve leaflets is also a function of the character of bending by the leaflet during the opening-closing cycle. Small radius bends, creases and intersecting creases, can produce high stress zones in the leaflet. These high stress zones can cause the formation of holes and tears under repetitive loading.

Bioprosthetic valves may be delivered using surgical or transcatheter techniques. A surgical valve is implanted into a patient using open-heart surgical techniques. The surgical valve is usually manufactured to have a fixed diameter as opposed to a transcatheter valve which is required to attain a range of diameters for access and delivery. The surgical valve is usually provided with a sewing cuff about a perimeter of the valve to allow for suturing to the native tissue orifice.

A preferred shape of synthetic heart valve leaflets has been described many times, but each is different from the others. The various three-dimensional shapes range from spherical or cylindrical to truncated conical intersections with spheres and an "alpharabola".

The shape most often described as preferable is modeled after the native human aortic valve. Though nature dictates the optimum shape for the native tissues to form a heart valve, we have discovered this is not true for synthetic materials; accordingly, the designs specified in the current disclosure are instead intended to place the synthetic materials under a minimized stress condition as compared to those based on copies of the native valve. This is partially accomplished through reduced buckling in the leaflet material.

SUMMARY

Described embodiments are directed to an apparatus, system, and methods for valve replacement, such as cardiac valve replacement. More specifically, described embodiments are directed toward flexible leaflet valve devices in which the leaflets are divided into zones, each with a particular geometry.

In accordance with an embodiment, a prosthetic valve comprises a plurality of leaflets, each leaflet defining two side regions and a central region between the side regions, the central region having a shape that is different from that of the side regions.

In accordance with an embodiment, a prosthetic valve comprises a leaflet frame and a film. The leaflet frame has a generally tubular shape. The leaflet frame defines a plurality of leaflet windows wherein each of the leaflet windows includes two leaflet window sides, a leaflet window base, and a leaflet window top. The film being coupled to the leaflet frame and defining at least one leaflet extending from each of the leaflet windows, wherein each leaflet has substantially the shape of an isosceles trapezoid having two leaflet sides, a leaflet base and a free edge opposite the leaflet base, wherein the two leaflet sides diverge from the leaflet base, and wherein the leaflet base is substantially flat. The leaflet base is coupled to the window base and each of the two leaflet sides are coupled to one of the two window sides.

In accordance with an embodiment, a prosthetic valve comprises a plurality of leaflets. Each leaflet includes a central region and two side regions on opposite sides of the central region. The central region is defined by a shape substantially that of an isosceles triangle defined by two central region sides, the leaflet base and the leaflet free edge, wherein the two central region sides converge from the leaflet base, and wherein each of the side regions have a shape substantially that of a triangle and each are defined by one of the central region sides, one of the leaflet sides, and the leaflet free edge.

In accordance with an embodiment, a method of forming a prosthetic heart valve comprises providing a leaflet frame having a generally tubular shape, the leaflet frame defining a plurality of leaflet windows wherein each of the leaflet windows includes two leaflet window sides, a leaflet window base, and a leaflet window top; providing a film, and wrapping the film about the leaflet frame bringing more than one layer of the film into contact with additional layers of the film defining at least one leaflet extending from each of the leaflet windows, wherein each leaflet has substantially the shape of an isosceles trapezoid having two leaflet sides, a leaflet base and a free edge opposite the leaflet base, wherein the two leaflet sides diverge from the leaflet base, wherein the leaflet base is substantially flat; wherein the leaflet base is coupled to the window base and wherein each of the two leaflet sides are coupled to one of the two window sides providing a generally annular support structure; and bonding the layers of film to itself and to the leaflet frame.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

DETAILED DESCRIPTION

Figure 1A:
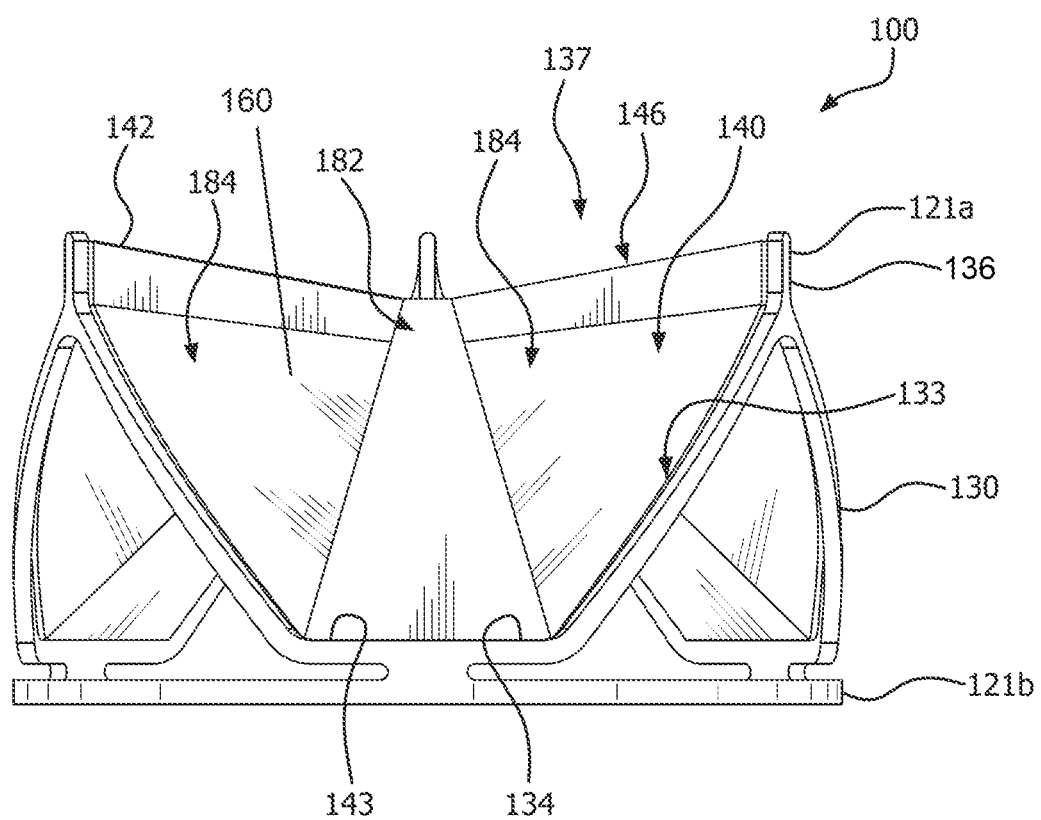
FIG. 1A is a side view of an embodiment of a valve.

Persons skilled in the art will readily appreciate that various aspects of the present disclosure can be realized by any number of methods and apparatus configured to perform the intended functions. Stated differently, other methods and apparatuses can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valves, more specifically cardiac prosthetic valves. However, embodiments within the scope of this disclosure can be applied toward any valve or mechanism of similar structure and/or function. Furthermore, embodiments within the scope of this disclosure can be applied in non-cardiac applications.

The term leaflet as used herein in the context of prosthetic valves is a component of a one-way valve wherein the leaflet is operable to move between an open and closed position under the influence of a pressure differential. In an open position, the leaflet allows blood to flow through the valve. In a closed position, the leaflet substantially blocks retrograde flow through the valve. In embodiments comprising multiple leaflets, each leaflet cooperates with at least one neighboring leaflet to block the retrograde flow of blood. The pressure differential in the blood is caused, for example, by the contraction of a ventricle or atrium of the heart, such pressure differential typically resulting from a fluid pressure building up on one side of the leaflets when closed. As the pressure on an inflow side of the valve rises above the pressure on the outflow side of the valve, the leaflets opens and blood flows therethrough. As blood flows through the valve into a neighboring chamber or blood vessel, the pressure on the inflow side equalizes with the pressure on the outflow side. As the pressure on the outflow side of the valve raises above the blood pressure on the inflow side of the valve, the leaflet returns to the closed position generally preventing retrograde flow of blood through the valve.

The term membrane as used herein refers to a sheet of material comprising a single composition, such as, but not limited to, expanded fluoropolymer.

The term composite material as used herein refers to a combination of a membrane, such as, but not limited to, expanded fluoropolymer, and an elastomer, such as, but not limited to, a fluoroelastomer. The elastomer may be imbibed within a porous structure of the membrane, coated on one or both sides of the membrane, or a combination of coated on and imbibed within the membrane.

The term laminate as used herein refers to multiple layers of membrane, composite material, or other materials, such as elastomer, and combinations thereof.

The term film as used herein generically refers to one or more of the membrane, composite material, or laminate.

The term biocompatible material as used herein generically refers to a film or a biological material, such as, but not limited to, bovine pericardium.

The term leaflet window is defined as that space that a leaflet frame defines, and from which a leaflet extends. The leaflet may extend from leaflet frame elements or adjacent to leaflet frame elements and spaced apart therefrom.

The terms native valve orifice and tissue orifice refer to an anatomical structure into which a prosthetic valve may be placed. Such anatomical structure includes, but is not limited to, a location wherein a cardiac valve may or may not have been surgically removed. It is understood that other anatomical structures that may receive a prosthetic valve include, but are not limited to, veins, arteries, ducts and shunts. Although reference is made herein to replacing a native valve with a prosthetic valve, it is understood and appreciated that a valve orifice or implant site may also refer to a location in a synthetic or biological conduit that may receive a valve for a particular purpose, and therefore the scope of the embodiments provided herein is not limited to valve replacement.

As used herein, "couple" means to join, couple, connect, attach, adhere, affix, or bond, whether directly or indirectly, and whether permanently or temporarily.

Embodiments herein include various apparatus, systems, and methods for a prosthetic valve suitable for surgical and transcatheter placement, such as, but not limited to, cardiac valve replacement. The valve is operable as a one-way valve wherein the valve defines a valve orifice into which leaflets open to permit flow and close so as to occlude the valve orifice and prevent flow in response to differential fluid pressure.

Embodiments provided herein are related to controlled leaflet opening. The durability of the valve leaflets is largely controlled by the character of bending exhibited by the leaflet during the opening-closing cycle. Small radius bends, creases and particularly intersecting creases, can produce high stress zones in the leaflet. These high stress zones can cause the formation of holes and tears under repetitive loading.

Controlled bending is of particular importance in thin, high-modulus synthetic leaflets, since the bending in these materials tends to be cellophane-like. If the leaflet bending character is uncontrolled, not only do creases form, but crease intersections lead to formation of large three dimensional structures that oppose bending and slow down the leaflet motion, both in opening and closing: in order to avoid this, the sequence of opening of the parts of the leaflet must be controlled.

Two basic physical properties have been recognized that largely control opening character; radius of zone curvature and area of zone. A planar zone moves sooner than a cylinder, which in turn moves earlier than a smaller radius cylinder, which moves earlier than a spherical zone and that a large planar zone moves earlier that a small one, and so on.

As will be described below, in some embodiments a leaflet comprises a flat base, wherein the leaflet bends from the base towards the leaflet free edge with minimal creasing and fluttering. In some embodiments the leaflet comprises a flat base that, among other things, provides for one or more of a shorter valve length, substantially prevents blood stagnation and pooling and encourages washing at the base, as compared to leaflets having a rounded base.

Valve

Figure 1B:
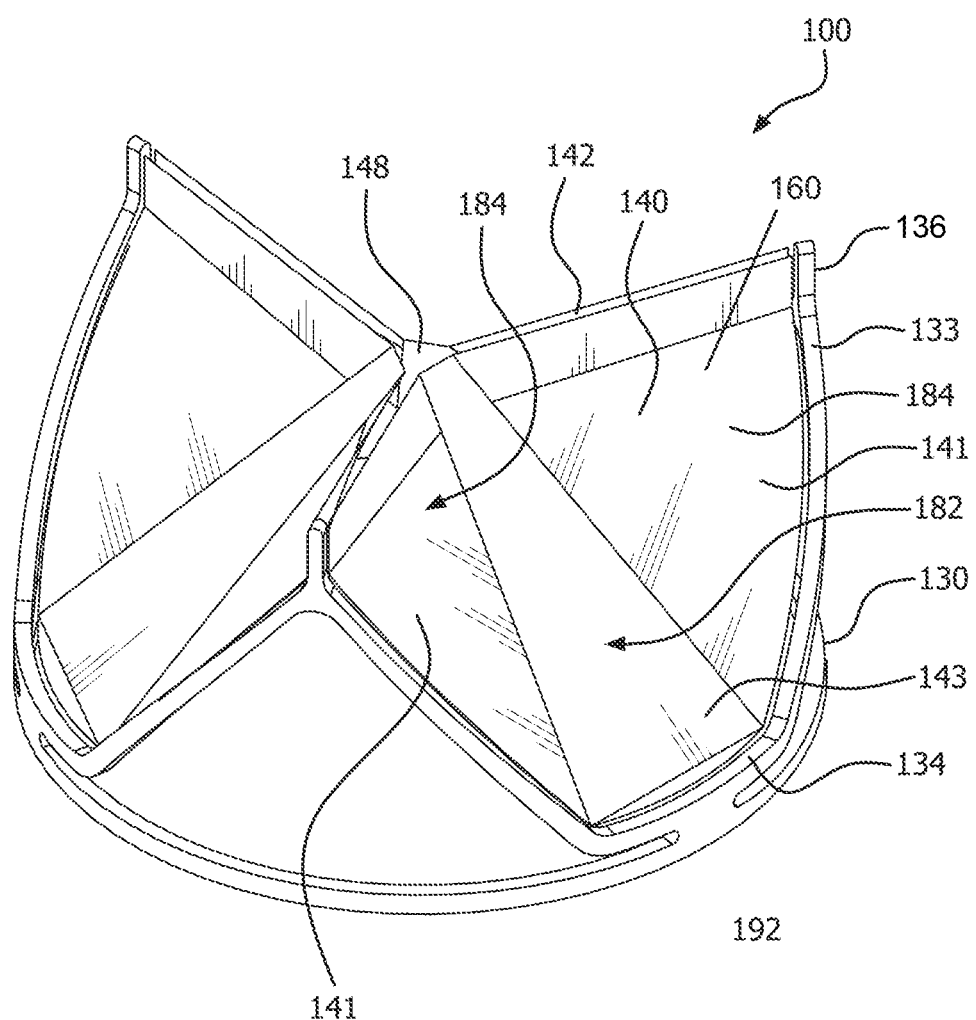
FIG. 1B is a perspective view of the embodiment of the valve of FIG. 1A.
Figure 2:
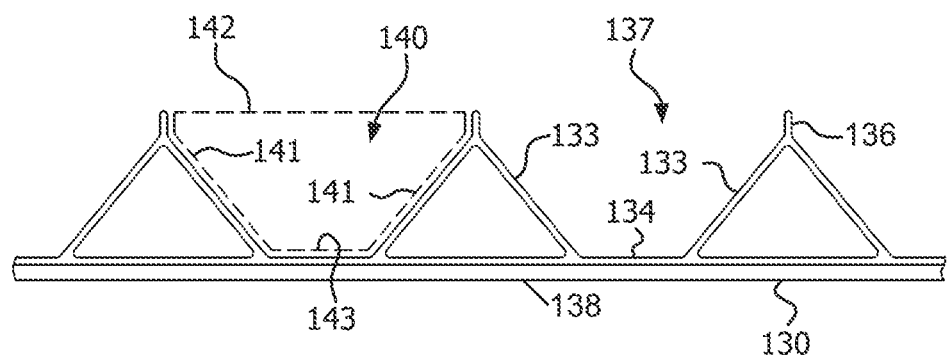
FIG. 2 is a representation of the embodiment of the valve of FIG. 1A unrolled to a flat orientation.
Figure 3A:
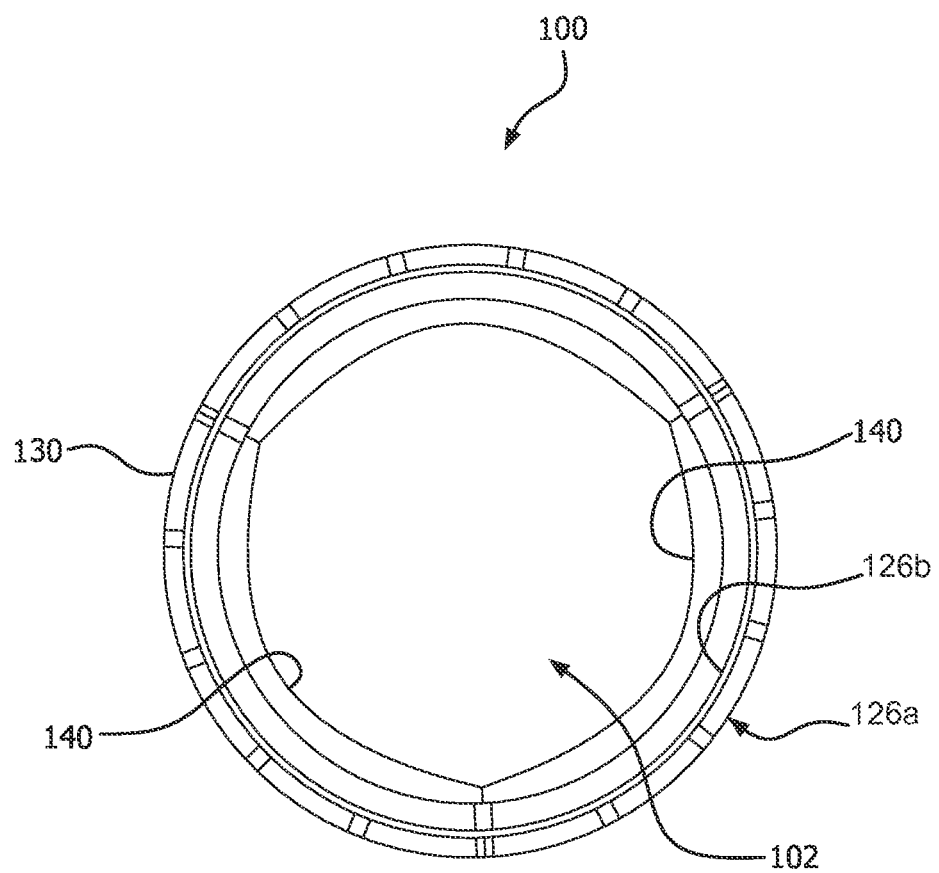
FIG. 3A is an axial or top view of the embodiment of the valve of FIG. 1A in an open configuration.
Figure 3B:
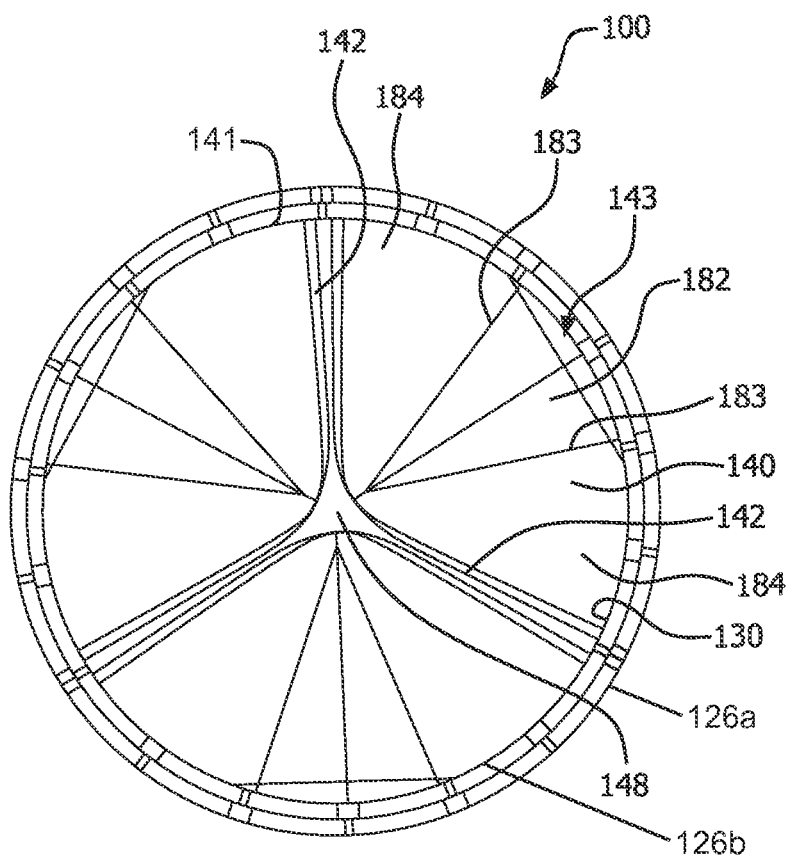
FIG. 3B is an axial or top view of the embodiment of the valve of FIG. 1A in a closed configuration.

FIG. 1A is a side view of a valve 100, in accordance with an embodiment. FIG. 1B is also a perspective view of the valve 100 of FIG. 1A. FIG. 2 is a side view of the valve 100 of FIG. 1A wherein the valve 100 has been longitudinally cut and laid open to better illustrate the elements of the generally tubular-shaped valve 100. FIGS. 3A and 3B are axial views of the valve 100 of FIG. 1A in an open and closed configuration, respectively. In FIGS. 1A, 1B and 3B the leaflets 140 are shown slightly open to better show the features but it is understood that a fully closed valve 100 will have the free edges 142 of the leaflets 140 coming together to coapt under the influence of downstream fluid pressure which results in closing the valve to prevent downstream blood from flowing retrograde through the valve.

Leaflet Frame

Referring to FIGS. 1A-2, the leaflet frame 130 is a generally tubular member. The leaflet frame 130 comprises a leaflet frame first end 121*a* and a leaflet frame second end 121*b* opposite the leaflet frame first end 121*a*. The leaflet frame 130 comprises a leaflet frame outer surface 126*a* and a leaflet frame inner surface 126*b* opposite the leaflet frame outer surface 126*a*, as shown in FIG. 3A. The leaflet frame 130 may comprise a structure known in the art as a stent. A stent is a tubular member that may have a small diameter suitable for percutaneous transcatheter delivery into the anatomy, and may be expanded to a larger diameter when deployed into the anatomy. Stents having various designs and material properties are well known in the art.

An open framework of the stent can define any number of features, repeatable or otherwise, such as geometric shapes and/or linear or meandering series of sinusoids. The leaflet frame 130 may comprise a cut tube, or any other element suitable for the particular purpose. The leaflet frame 130 may be etched, cut, laser cut, or stamped into a tube or a sheet of material, with the sheet then formed into a substantially cylindrical structure. Alternatively, an elongated material, such as a wire, bendable strip, or a series thereof, can be bent or braided and formed into a substantially cylindrical structure wherein the walls of the cylinder comprise an open framework.

The leaflet frame 130 can comprise any metallic or polymeric biocompatible material. For example, the leaflet frame 130 can comprise a material, such as, but not limited to nitinol, cobalt-nickel alloy, stainless steel, or polypropylene, acetyl homopolymer, acetyl copolymer, ePTFE, other alloys or polymers, or any other biocompatible material having adequate physical and mechanical properties to function as described herein.

Figure 4A:
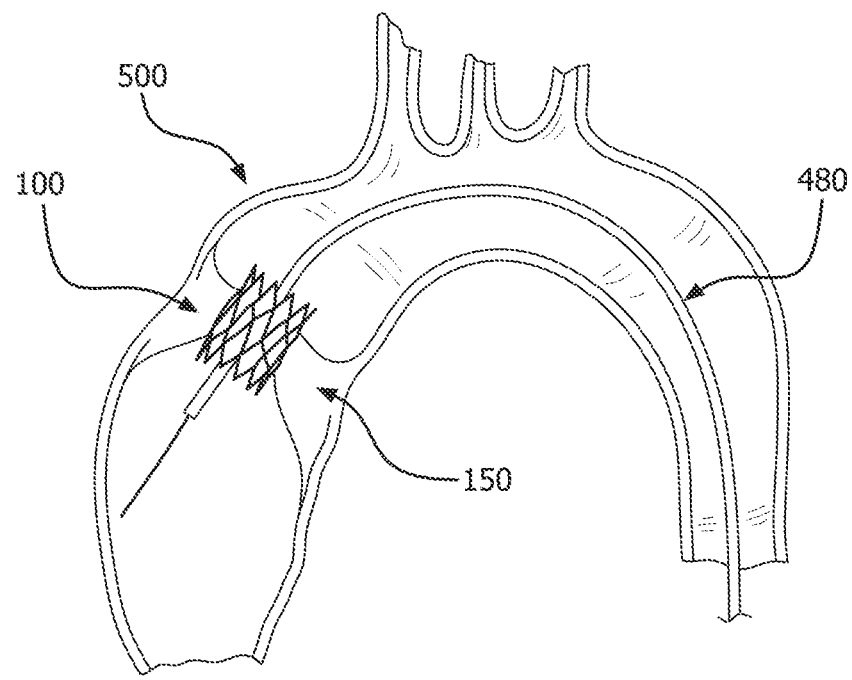
FIG. 4A is a side view of an embodiment of a transcatheter delivery system within anatomy.

In accordance with embodiments, the leaflet frame 130 can be configured to provide positive engagement with an implant site to firmly anchor the valve 100 to the site, as shown in FIG. 4A representing a transcatheter deployment of the valve 100. In accordance with an embodiment, the leaflet frame 130 can comprise a sufficiently rigid frame having small elastic recoil so as to maintain sufficient apposition against a tissue orifice 150 to maintain position. In accordance with another embodiment, the leaflet frame 130 can be configured to expand to a diameter that is larger than a tissue orifice 150 so that when valve 100 expands into the tissue orifice 150, it can be firmly seated therein. In accordance with another embodiment, the leaflet frame 130 can comprise one or more anchors (not shown) configured to engage the implant site, such as a tissue orifice 150, to secure the valve 100 to the implant site.

It is appreciated that other elements or means for coupling the valve 100 to an implant site are anticipated. By way of example, but not limited thereto, other means, such as mechanical and adhesive means may be used to couple the valve 100 to a synthetic or biological conduit.

As will be discussed later, a valve 100 suitable for surgical implantation may or may not have the zigzag configuration since the valve 100 may be of a fixed diameter and need not be operable to compress and re-expand.

Referring to FIG. 2, the leaflet frame comprises a plurality of spaced apart leaflet frame elements defining substantially an isosceles triangle interconnected by a base element 138 defining leaflet windows 137 defining a shape of an isosceles trapezoid. Each leaflet window side 133 is defined by a side of one triangle and a side of an adjacent triangle, and wherein each leaflet window base 134 is defined by the base element 138.

Referring again to FIGS. 1A and 2, the leaflet frame first end 121*a* further comprises posts 136 extending from an apex of the leaflet frame elements defining substantially an isosceles triangle. The post 136 may affect the leaflet free edge 142 so as to create a larger or wider coaptation region 146 between adjacent leaflet free edges 142.

Figure 5:
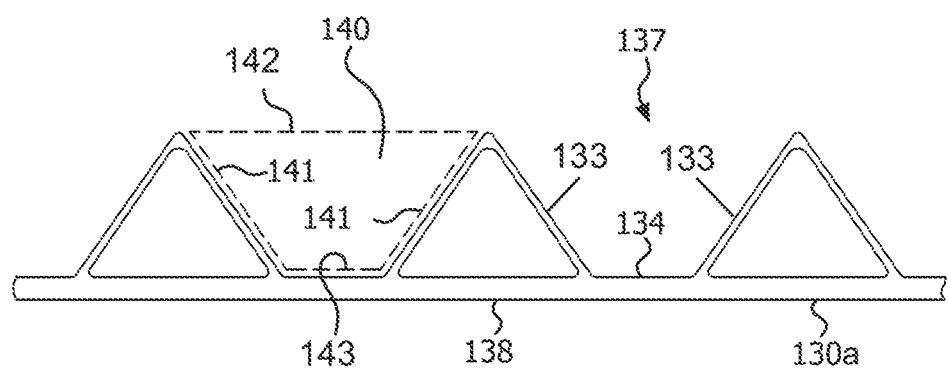
FIG. 5 is a representation of an embodiment of a leaflet frame unrolled to a flat orientation.

FIG. 5 is a representation of another embodiment of a leaflet frame 130*a* unrolled to a flat orientation. The leaflet frame 130 is substantially the same as the embodiment of FIG. 2 but without the posts 136.

In accordance with an embodiment, the frame 130 comprises a frame having a shape determined, at least in part, by wrapping a two dimensional isosceles trapezoid onto the tubular shape of the frame 130, the isosceles trapezoid having a base 134 and two sides 133 that diverge from the base 134, and wherein a side 133 from adjacent isosceles trapezoids meet at the frame first end 121a, as shown in FIGS. 2 and 5. A leaflet 140 is shown in dotted line to represent where the leaflet 143 is located within the leaflet window 137, the leaflet window 137 being defined by the leaflet window sides 133 and the leaflet window base 134.

Sewing Cuff

Figure 4B:
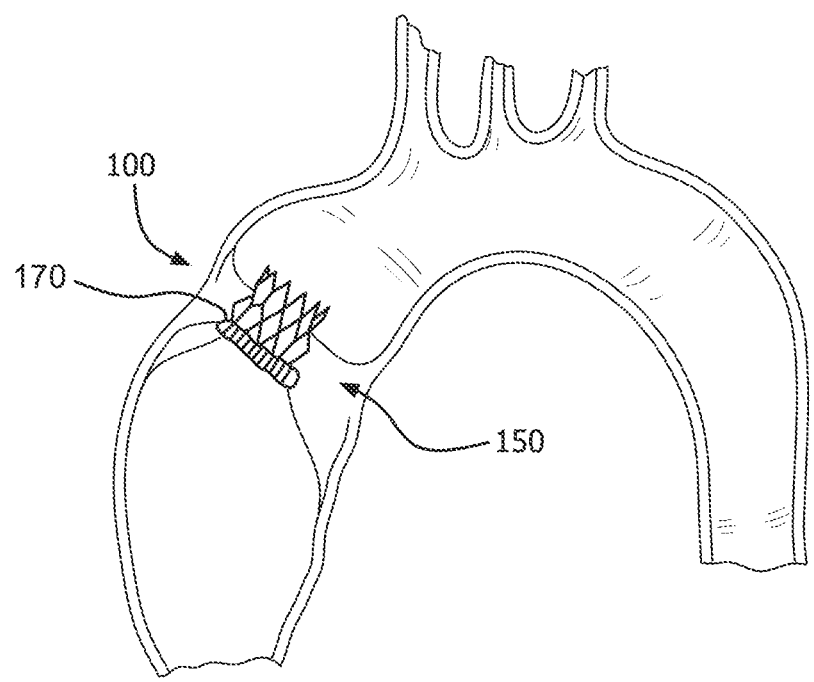
FIG. 4B is a side view of an embodiment of a surgical valve within anatomy.

In accordance with a valve 100 embodiment suitable for surgical implantation, the valve 100 further comprises a sewing cuff 170 about a leaflet frame outer surface 137 in accordance with an embodiment, as shown in FIG. 4B. The sewing cuff 170 is operable to provide structure that receives suture for coupling to the implant site. The sewing cuff 170 may comprise any suitable material, such as, but not limited to, double velour polyester. The sewing cuff 170 may be located circumferentially around a perimeter of the leaflet frame 130. Sewing cuffs are known in the art.

Film

The film 160 is generally any sheet-like material that is biologically compatible and configured to couple to leaflets 140 to the leaflet frame 130, in accordance with embodiments. It is understood that the term "film" is used generically for one or more biocompatible materials suitable for a particular purpose. The leaflets 140 are also comprised of the film 160.

In accordance with an embodiment, the biocompatible material is a film 160 that is not of a biological source and that is sufficiently flexible and strong for the particular purpose, such as a biocompatible polymer. In an embodiment, the film 160 comprises a biocompatible polymer that is combined with an elastomer, referred to as a composite.

In an embodiment, the film 160 may be formed from a generally tubular material to at least partially cover the leaflet frame 130 and the leaflet frame 130. The film 160 can comprise one or more of a membrane, composite material, or laminate. Details of various types of film 160 are discussed below.

Leaflet

Referring to FIGS. 1A and 2, each leaflet window 137 is provided with a biocompatible material, such as a film 160, which is coupled to a portion of the leaflet window sides 133 with the film 160 defining a leaflet 140. Each leaflet 140 defines a leaflet free edge 142 and a leaflet base 143, in accordance with an embodiment. As will be described below, it is anticipated that a plurality of embodiments of leaflet base configurations may be provided. In accordance with an embodiment, the film 160 is coupled to a portion of the leaflet window sides 133 and to the leaflet window base 134 where the leaflet 140 is defined by the portion of the leaflet window sides 133 and to the leaflet window base 134.

The shape of the leaflets 140 are defined in part by the shape of the leaflet window 137 and the leaflet free edge 142. When the leaflets 140 are in a fully open position, the valve 100 presents a substantially circular valve orifice 102 as shown in FIG. 3A. Fluid flow is permitted through the valve orifice 102 when the leaflets 140 are in an open position.

As the leaflets 140 cycle between the open and closed positions, the leaflets 140 generally flex about the leaflet base 143 and the portion of the leaflet window sides 133 to which the leaflet are coupled. When the valve 100 is closed, generally about half of each leaflet free edge 142 abuts an adjacent half of a leaflet free edge 142 of an adjacent leaflet 140, as shown in FIG. 3B. The three leaflets 140 of the embodiment of FIG. 3B meet at a triple point 148. The valve orifice 102 is occluded when the leaflets 140 are in the closed position stopping fluid flow.

Referring to FIG. 3B, in accordance with an embodiment, each leaflet 140 includes a central region 182 and two side regions 184 on opposite sides of the central region 182. The central region 182 is defined by a shape substantially that of an isosceles triangle defined by two central region sides 183, the leaflet base 143 and the free edge 142. The two central region sides 183 converge from the leaflet base 143 to the free edge 142. Each of the side regions 184 have a shape substantially that of a triangle and each are defined by one of the central region sides 183, one of the leaflet sides 141, and the free edge 142.

In accordance with an embodiment, each of the two side regions 184 and the central region 182 are substantially planar when the valve 100 is in the closed position and under no pressure load.

The leaflet 140 can be configured to actuate at a pressure differential in the blood caused, for example, by the contraction of a ventricle or atrium of the heart, such pressure differential typically resulting from a fluid pressure building up on one side of the valve 100 when closed. As the pressure on an inflow side of the valve 100 rises above the pressure on the outflow side of the valve 100, the leaflet 140 opens and blood flows therethrough. As blood flows through the valve 100 into a neighboring chamber or blood vessel, the pressure equalizes. As the pressure on the outflow side of the valve 100 rises above the blood pressure on the inflow side of the valve 100, the leaflet 140 returns to the closed position generally preventing the retrograde flow of blood through the inflow side of the valve 100.

It is understood that the leaflet frame 130 may comprise any number of leaflet windows 137, and thus leaflets 140, suitable for a particular purpose, in accordance with embodiments. Leaflet frames 130 comprising one, two, three or more leaflet windows 137 and corresponding leaflets 140 are anticipated.

Leaflet Film

The biocompatible material that makes up the leaflet 140 can comprise any biological tissue or synthetic, biocompatible materials sufficiently compliant and flexible, such as a biocompatible polymer. In an embodiment, the leaflet 140 comprises a biocompatible polymer that is combined with an elastomer, referred to as a composite. A material according to one embodiment includes a composite material comprising an expanded fluoropolymer membrane, which comprises a plurality of spaces within a matrix of fibrils, and an elastomeric material. It should be appreciated that multiple types of fluoropolymer membranes and multiple types of elastomeric materials can be combined to form a laminate while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In accordance with an embodiment, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, may comprise PTFE homopolymer. In alternative embodiments, blends of PTFE, expandable modified PTFE and/or expanded copolymers of PTFE may be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure for achieving the desired leaflet performance. In accordance with an embodiment, the expanded fluoropolymer comprises a microstructure of nodes interconnected by fibrils, such as described in U.S. Pat. No. 3,953,566 to Gore. The fibrils radially extend from the nodes in a plurality of directions, and the membrane has a generally homogeneous structure. Membranes having this microstructure may typically exhibit a ratio of matrix tensile strength in two orthogonal directions of less than 2, and possibly less than 1.5.

In another embodiment, the expanded fluoropolymer membrane has a microstructure of substantially only fibrils, as is generally taught by U.S. Pat. No. 7,306,729, to Bacino. The expanded fluoropolymer membrane having substantially only fibrils, can possess a high surface area, such as greater than 20 $m^2/g$, or greater than 25 $m^2/g$, and in some embodiments can provide a highly balanced strength material having a product of matrix tensile strengths in two orthogonal directions of at least $1.5 \times 10^5$ $MPa^2$, and/or a ratio of matrix tensile strengths in two orthogonal directions of less than 4, and possibly less than 1.5.

The expanded fluoropolymer membrane can be tailored to have any suitable thickness and mass to achieve the desired leaflet performance. By way of example, but not limited thereto, the leaflet 140 comprises an expanded fluoropolymer membrane having a thickness of about 0.1 μm. The expanded fluoropolymer membrane can possess a mass per area of about 1.15 $g/m^2$. Membranes according to an embodiment of the invention can have matrix tensile strengths of about 411 MPa in the longitudinal direction and 315 MPa in the transverse direction.

Additional materials may be incorporated into the pores or within the material of the membranes or in between layers of membranes to enhance desired properties of the leaflet. Composite materials described herein can be tailored to have any suitable thickness and mass to achieve the desired leaflet performance. Composite materials according to embodiments can include fluoropolymer membranes and have a thickness of about 1.9 μm and a mass per area of about 4.1 $g/m^2$.

The expanded fluoropolymer membrane combined with elastomer to form a composite material provides the elements of the present disclosure with the performance attributes required for use in high-cycle flexural implant applications, such as heart valve leaflets, in various ways. For example, the addition of the elastomer can improve the fatigue performance of the leaflet by eliminating or reducing the stiffening observed with ePTFE-only materials. In addition, it may reduce the likelihood that the material will undergo permanent set deformation, such as wrinkling or creasing, that could result in compromised performance. In one embodiment, the elastomer occupies substantially all of the pore volume or space within the porous structure of the expanded fluoropolymer membrane. In another embodiment the elastomer is present in substantially all of the pores of the at least one fluoropolymer layer. Having elastomer filling the pore volume or present in substantially all of the pores reduces the space in which foreign materials can be undesirably incorporated into the composite. An example of such foreign material is calcium that may be drawn into the membrane from contact with the blood. If calcium becomes incorporated into the composite material, as used in a heart valve leaflet, for example, mechanical damage can occur during cycling open and closed, thus leading to the formation of holes in the leaflet and degradation in hemodynamics.

In an embodiment, the elastomer that is combined with the ePTFE is a thermoplastic copolymer of tetrafluoroethylene (TFE) and perfluoromethyl vinyl ether (PMVE), such as described in U.S. Pat. No. 7,462,675 to Chang et al. As discussed above, the elastomer is combined with the expanded fluoropolymer membrane such that the elastomer occupies substantially all of the void space or pores within the expanded fluoropolymer membrane to form a composite material. This filling of the pores of the expanded fluoropolymer membrane with elastomer can be performed by a variety of methods. In one embodiment, a method of filling the pores of the expanded fluoropolymer membrane includes the steps of dissolving the elastomer in a solvent suitable to create a solution with a viscosity and surface tension that is appropriate to partially or fully flow into the pores of the expanded fluoropolymer membrane and allow the solvent to evaporate, leaving the filler behind.

In one embodiment, the composite material comprises three layers: two outer layers of ePTFE and an inner layer of a fluoroelastomer disposed therebetween. Additional fluoroelastomers can be suitable and are described in U.S. Publication No. 2004/0024448 to Chang et al.

In another embodiment, a method of filling the pores of the expanded fluoropolymer membrane includes the steps of delivering the filler via a dispersion to partially or fully fill the pores of the expanded fluoropolymer membrane.

In another embodiment, a method of filling the pores of the expanded fluoropolymer membrane includes the steps of bringing the porous expanded fluoropolymer membrane into contact with a sheet of the elastomer under conditions of heat and/or pressure that allow elastomer to flow into the pores of the expanded fluoropolymer membrane.

In another embodiment, a method of filling the pores of the expanded fluoropolymer membrane includes the steps of polymerizing the elastomer within the pores of the expanded fluoropolymer membrane by first filling the pores with a prepolymer of the elastomer and then at least partially curing the elastomer.

After reaching a minimum percent by weight of elastomer, the leaflets constructed from fluoropolymer materials or ePTFE generally performed better with increasing percentages of elastomer resulting in significantly increased cycle lives. In one embodiment, the elastomer combined with the ePTFE is a thermoplastic copolymer of tetrafluoroethylene and perfluoromethyl vinyl ether, such as described in U.S. Pat. No. 7,462,675 to Chang et al., and other references that would be known to those of skill in the art. Other biocompatible polymers which can be suitable for use as a leaflet include but are not limited to the groups of urethanes, silicones(organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

Other Considerations

In accordance with an embodiment, the valve 100 can be configured to prevent interference with a heart conduction system by not covering the bundle branch in the left ventricle when implanted, such as might be encountered with an aortic valve replacement procedure. For example, the valve 100 can comprise a length of less than about 25 mm or less than about 18 mm. The valve 100 can also comprise an aspect ratio of less than one, wherein the ratio describes the relationship between the length of the valve 100 to the expanded, functional diameter. However, the valve 100 can be constructed at any length and, more generally, any desirable dimension.

In accordance with an embodiment of a valve 100 suitable for transcatheter delivery the valve 100 may be compressed into a collapsed configuration having a smaller diameter and expanded into an expanded configuration so that the valve 100 can be delivered via catheter in the collapsed configuration and expanded upon deployment within the tissue orifice 150 as shown in FIG. 4A. The leaflet frame 130 can be operable to recover circumferential uniformity when transitioning from the collapsed configuration to the expanded configuration.

The valve 100 can further comprise a bio-active agent. Bio-active agents can be coated onto a portion or the entirety of the film 160 for controlled release of the agents once the valve 100 is implanted. The bio-active agents can include, but are not limited to, vasodilator, anti-coagulants, anti-platelet, anti-thrombogenic agents such as, but not limited to, heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Transcatheter Delivery System

In an embodiment, with reference to FIG. 4A, a valve delivery system 500 comprises a valve 100 having a collapsed configuration and an expanded configuration as previously described and an elongated flexible catheter 480, such as a balloon catheter, configured to deploy the valve 100 via catheter. The catheter 480 can comprise a balloon to expand the valve 100 and/or if required, to touch up the valve 100 to ensure proper seating. The valve 100 can be mounted to the distal section of the catheter 480 for delivery through the vasculature. In order to hold the valve in a collapsed configuration on the catheter 480, the valve delivery system may further comprise a removable sheath (not shown) to closely fit over the transcatheter valve 100.

A method of delivery can comprise the steps of radially compressing a valve into its collapsed configuration onto the distal end of an elongate flexible catheter having proximal and distal ends; delivering the valve to a tissue orifice, such as a native aortic valve orifice, via a transfemoral or transapical route, and expanding the valve into the tissue orifice. The valve can be expanded by inflating a balloon.

A method of delivery can comprise the steps of radially compressing a valve into its collapsed configuration, onto the distal section of an elongated flexible catheter having proximal and distal ends. A restraint, which can be connected to a tether that passes through the orifice of valve and the lumen of the catheter, is fitted around the posts of the valve. The valve is then delivered to a native valve orifice, such as a native aortic valve orifice, via a route of delivery and expanded into the native orifice. The route of delivery can comprise a transfemoral or transapical route. The valve can be expanded by inflating a balloon.

Surgical Embodiments

It is appreciated that the embodiments of the valve 100 may be surgically implanted rather than using transcatheter techniques. Embodiments of a surgically implanted valve 100 may be substantially the same as those described above, with the addition of a sewing cuff adjacent to the leaflet frame outer surface 126a, shown in FIG. 4B, in accordance with an embodiment. The sewing cuff, which is well known in the art, is operable to provide structure that receives suture for coupling the valve 100 to an implant site, such as the tissue orifice. The sewing cuff may comprise any suitable material, such as, but not limited to, double velour polyester. The sewing cuff may be located circumferentially around the base of the leaflet frame 130 or perivalvular depending from the leaflet frame.

Method of Making

Figure 6:
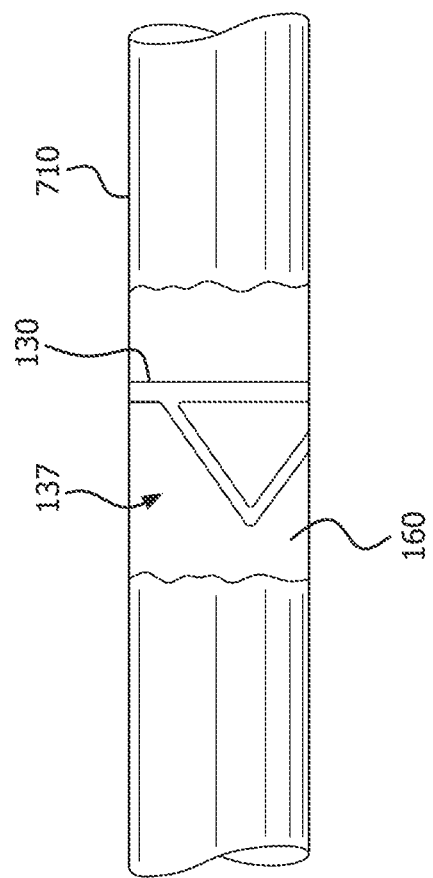
FIG. 6 is a side view of the leaflet frame on an assembly mandrel, in accordance with an embodiment.
Figures 7A, 7B:
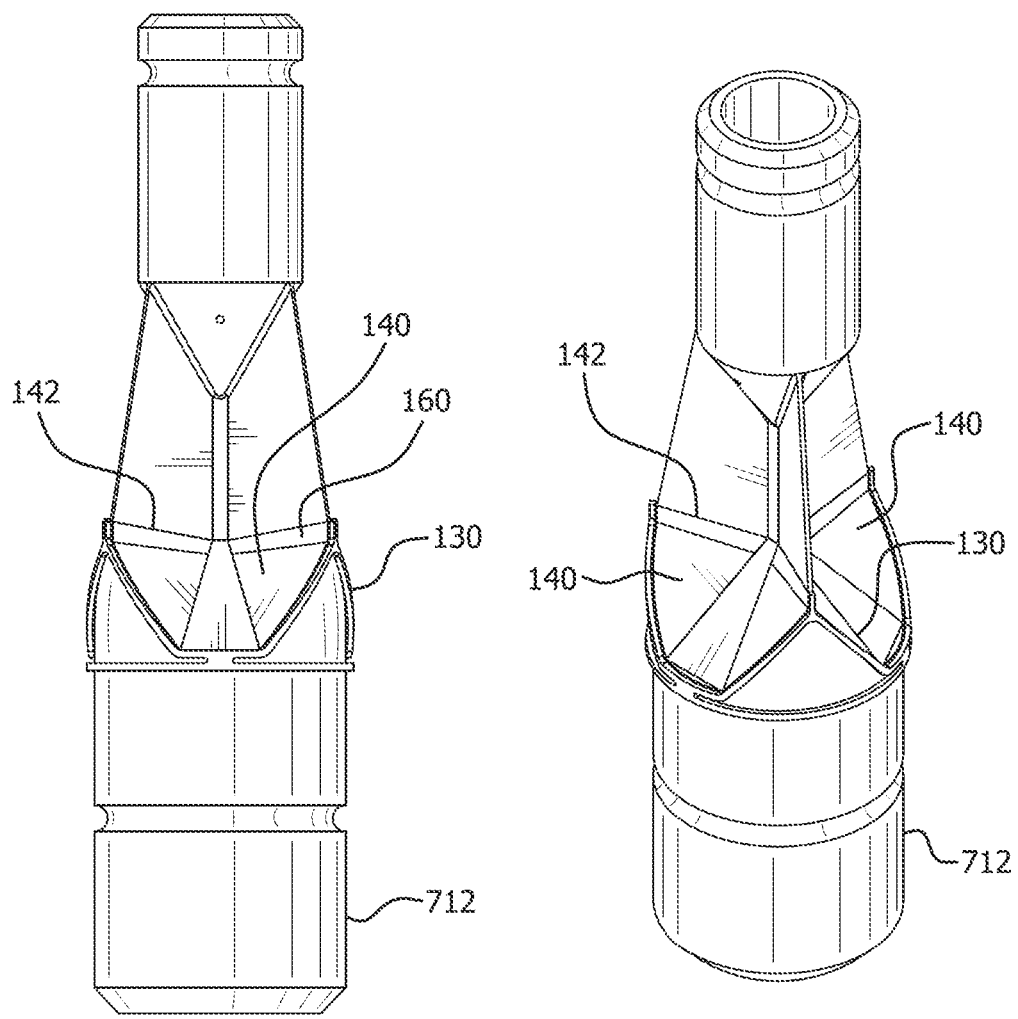
FIG. 7A is a side view of the leaflet frame on a cutting mandrel, in accordance with an embodiment.
FIG. 7B is a perspective view of the leaflet frame on the cutting of FIG. 7A.

Embodiments described herein also pertain to a method of making the valve 100 embodiments as described herein. In order to make the various embodiments, a cylindrical mandrel 710 can be used. With reference to FIG. 6, the mandrel 710 comprises a structural form operable to receive the leaflet frame 130 thereon. An embodiment of a method of making a valve 100 comprises the steps of wrapping a first layer of film 160, e.g., a composite as described herein, into a tubular form about the mandrel 710; placing the leaflet frame 130 over the first layer of film 160, as shown in FIG. 6; forming a second layer of film 160 over the leaflet frame 130; thermally setting the assembly; receiving the assembly over a cutting mandrel 712 as shown in FIGS. 7A and 7B; cutting the film 160 across the leaflet window top within the leaflet window 137.

Example

In exemplary embodiments, a heart valve having polymeric leaflets formed from a composite material having an expanded fluoropolymer membrane and an elastomeric material and joined to a semi-rigid, non-collapsible metallic frame, and further a having strain relief was constructed according to the following process:

A leaflet frame 130 was laser machined from a length of MP35N cobalt chromium tube hard tempered with an outside diameter of 26.0 mm and a wall thickness of 0.6 mm in the shape. The leaflet frame was electro-polished resulting in 0.0127 mm material removal from each surface and leaving the edges rounded. The leaflet frame was exposed to a surface roughening step to improve adherence of leaflets to the leaflet frame. The leaflet frame was cleaned by submersion in an ultrasonic bath of acetone for approximately five minutes. The entire metal frame surface was then subjected to a plasma treatment using equipment (e.g. PVA TePLa America, Inc Plasma Pen, Corona, CA) and methods commonly known to those having ordinary skill in the art. This treatment also served to improve the wetting of the fluorinated ethylene propylene (FEP) adhesive.

FEP powder (Daikin America, Orangeburg N.Y.) was then applied to the leaflet frame. More specifically, the FEP powder was stirred to form an airborne "cloud" in an enclosed blending apparatus, such as a standard kitchen type blender, while the leaflet frame is suspended in the cloud. The leaflet frame was exposed to the FEP powder cloud until a layer of powder was adhered to the entire surface of the leaflet frame. The leaflet frame was then subjected to a thermal treatment by placing it in a forced air oven set to 320° C. for approximately three minutes. This caused the powder to melt and adhere as a thin coating over the entire leaflet frame. The leaflet frame was removed from the oven and left to cool to approximately room temperature.

The strain relief was attached to the leaflet frame in the following manner. A thin (122 μm) walled sintered 15 mm diameter ePTFE tube was disposed on a 24.5 mm vented metal mandrel by stretching radially over a tapered mandrel. Two layers of a substantially nonporous ePTFE membrane with a continuous FEP coating was circumferentially wrapped on the mandrel with the FEP side towards the mandrel. The wrapped mandrel was placed in a convection oven set to 320° C. and heated for 20 min. The ePTFE and substantially nonporous ePTFE membrane combined to serve as an inner release liner and was perforated using a scalpel blade to communicate pressure between the vent holes in the mandrel. This entire release liner is removed in a later step.

A 5 cm length of the thick (990μ) walled partially sintered 22 mm inner diameter ePTFE tube (density=0.3 g/cm³) was disposed onto the 24.5 mm vented metal mandrel with release liner. The ePTFE tube inner diameter was enlarged by stretching it on a tapered mandrel to accommodate the larger mandrel diameter.

A thin (4 μm) film of type 1 FEP (ASTM D3368) was constructed using melt extrusion and stretching. One layer of the FEP was wrapped over the 5 cm length of the ePTFE tube.

The FEP powder coated leaflet frame was disposed onto the vented metal mandrel generally in the middle of the 5 cm span of ePTFE tube and FEP film.

One layer of the FEP was wrapped over the leaflet frame and 5 cm length of the ePTFE tube.

A second 5 cm length of the 990 μm thick/22 mm inner diameter ePTFE tube was disposed onto the assembly layered onto 24.5 mm vented metal mandrel by stretching its radius over a tapered mandrel to accommodate the larger construct diameter.

A substantially nonporous ePTFE membrane was configured into a cylinder at a diameter larger than the construct and placed over the assembly, referred to as sacrificial tube. Sintered ePTFE fiber (e.g. Gore® Rastex® Sewing Thread, Part #S024T2, Newark DE) was used to seal both ends of the sacrificial tube against the mandrel.

The assembly, including the mandrel, was heated in a convection oven (temperature set point of 390° C.) capable of applying pneumatic pressure of 100 psi external to the sacrificial tube described above while maintaining a vacuum internal to the mandrel. The assembly was cooked for 40 min such that the mandrel temperature reached approximately 360° C. (as measured by a thermocouple direct contact with the inner diameter of the mandrel). The assembly was removed from the oven and allowed to cool to approximately room temperature while still under 100 psi pressure and vacuum.

The sacrificial tube was then removed. Approximately 30 psi of pressure was applied to the internal diameter of the mandrel to assist in removal of the assembly. The inner release liner was peeled away from the internal diameter of the assembly by inverting the liner and axially pulling it apart.

The polymeric material was trimmed with a scalpel and removed from the leaflet windows and bottom of the leaflet frame leaving approximately 0.5 to 1.0 mm of material overhang.

A leaflet material was then prepared. A membrane of ePTFE was manufactured according to the general teachings described in U.S. Pat. No. 7,306,729. The ePTFE membrane had a mass per area of 0.452 g/m², a thickness of about 508 nm, a matrix tensile strength of 705 MPa in the longitudinal direction and 385 MPa in the transverse direction. This membrane was imbibed with a fluoroelastomer. The copolymer consists essentially of between about 65 and 70 weight percent perfluoromethyl vinyl ether and complementally about 35 and 30 weight percent tetrafluoroethylene.

The fluoroelastomer was dissolved in Novec HFE7500 (3M, St Paul, MN) in a 2.5% concentration. The solution was coated using a mayer bar onto the ePTFE membrane (while being supported by a polypropylene release film) and dried in a convection oven set to 145° C. for 30 seconds. After 2 coating steps, the final ePTFE/fluoroelastomer or composite had a mass per area of 1.75 g/m², 29.3% fluoropolymer by weight, a dome burst strength of about 8.6 KPa, and thickness of 0.81 μm.

The final leaflet was comprised of 28.22% fluoropolymer by weight with a thickness of 50.3 μm. Each leaflet had 26 layers of the composite and a ratio of thickness/number of layers of 1.93 μm.

The resulting valve included leaflets formed from a composite material with more than one fluoropolymer layer having a plurality of pores and an elastomer present in substantially all of the pores of the more than one fluoropolymer layer. Each leaflet was movable between a closed position, shown illustratively in FIG. 3B, in which fluid was substantially prevented from flowing through the valve, and an open position, shown illustratively in FIG. 3A, in which fluid was allowed to flow through the valve.

The performance of the valve leaflets was characterized on a real-time pulse duplicator that measured typical anatomical pressures and flows across the valve. The flow performance was characterized by the following process:

The valve assembly was potted into a silicone annular ring (support structure) to allow the valve assembly to be subsequently evaluated in a real-time pulse duplicator. The potting process was performed according to the recommendations of the pulse duplicator manufacturer (ViVitro Laboratories Inc., Victoria BC, Canada)

The potted valve assembly was then placed into a real-time left heart flow pulse duplicator system. The flow pulse duplicator system included the following components supplied by VSI Vivitro Systems Inc., Victoria BC, Canada: a Super Pump, Servo Power Amplifier Part Number SPA 3891; a Super Pump Head, Part Number SPH 5891B, 38.320 cm² cylinder area; a valve station/fixture; a Wave Form Generator, TriPack Part Number TP 2001; a Sensor Interface, Part Number VB 2004; a Sensor Amplifier Component, Part Number AM 9991; and a Square Wave Electro Magnetic Flow Meter, Carolina Medical Electronics Inc., East Bend, NC, USA.

In general, the flow pulse duplicator system uses a fixed displacement, piston pump to produce a desired fluid flow through the valve under test.

The heart flow pulse duplicator system was adjusted to produce the desired flow (5 L/min), mean pressure (15 mmHg), and simulated pulse rate (70 bpm). The valve under test was then cycled for about 5 to 20 minutes.

Pressure and flow data were measured and collected during the test period, including right ventricular pressures, pulmonary pressures, flow rates, and pump piston position. Parameters used to characterize the valve are effective orifice area and regurgitant fraction. The effective orifice area (EOA), which can be calculated as follows: $EOA(cm^2) = Q_{ms}/(51.6*(\Delta P)^{1/2})$ where $Q_{ms}$ is the root mean square systolic/diastolic flow rate (cm³/s) and $\Delta P$ is the mean systolic/diastolic pressure drop (mmHg).

Another measure of the hydrodynamic performance of a valve is the regurgitant fraction, which is the amount of fluid or blood regurgitated through the valve divided by the stroke volume.

The hydrodynamic performance was measured prior to accelerated wear testing. The performance values were; EOA=2.4 cm² and regurgitant fraction=11.94%.

It will be apparent to those skilled in the art that various modifications and variations can be made in the present embodiments without departing from the spirit or scope of the embodiments. Thus, it is intended that the present embodiments cover the modifications and variations of this invention provided they come within the scope of the appended claims and their equivalents.

What is claimed:

1. A prosthetic valve, comprising:
a plurality of leaflets, wherein each leaflet includes a central region and two side regions on opposite sides of the central region, wherein the central region has a shape substantially that of an isosceles triangle and is defined by two central region sides, a leaflet base, and a leaflet free edge, wherein the two central region sides converge from the leaflet base toward the leaflet free edge, and wherein each of the two side regions has a shape substantially that of a triangle and is defined by one of the central region sides, one of first or second leaflet sides, and the leaflet free edge, wherein the leaflet base comprises a linear portion; and a frame having a plurality of spaced apart leaflet frame elements defining a plurality of leaflet windows, wherein each leaflet window comprises a leaflet window base and first and second leaflet window sides that diverge from the leaflet window base;

wherein one of the leaflets is located within each of the windows, wherein the first leaflet side is coupled along its length to the first leaflet window side and the second leaflet side is coupled along its length to the second leaflet window side, and wherein the leaflet base is coupled along its length to the leaflet window base.

2. The prosthetic valve of claim 1, wherein each of the two side regions and the central region are substantially planar when the prosthetic valve is in a closed position and in a non-pressurized condition.

3. The prosthetic valve of claim 1, wherein each leaflet is defined by a film provided with a biocompatible material, the film being coupled to a portion of each of the first and second leaflet window sides.

4. The prosthetic valve of claim 1, wherein the frame comprises a cut tube; or wherein the frame is etched, laser cut or stamped into a sheet material, and formed into a cylindrical structure; or wherein the frame is formed from a bent or braided elongate material formed into a substantially cylindrical structure.

5. The prosthetic valve of claim 1, wherein the frame comprises one or more anchors configured to engage an implant site and secure the valve thereto, in use.

6. The prosthetic valve of claim 1, wherein the frame comprises a metallic or polymeric biocompatible material.

7. The prosthetic valve of claim 1, wherein each of the leaflets comprises a biocompatible polymer.

8. The prosthetic valve of claim 7, wherein each of the leaflets comprises a composite formed from a biocompatible polymer combined with an elastomer.

9. The prosthetic valve of claim 8, wherein the composite comprises a porous ePTFE membrane.

10. The prosthetic valve of claim 9, wherein the elastomer is a copolymer of tetrafluoroethylene and perfluoromethyl vinyl ether.

11. The prosthetic valve of claim 8, wherein the elastomer is present in substantially all pores of the ePTFE membrane.

12. The prosthetic valve of claim 1, wherein the valve is a prosthetic heart valve.

13. The prosthetic valve of claim 1, wherein the length of the leaflet window base extends along a plane that that is transverse to a longitudinal axis of the frame.

14. The prosthetic valve of claim 1, wherein the leaflet base further comprises flat portion that is transverse relative to a longitudinal axis of the frame, the flat portion extending from an attachment portion to the linear portion, and wherein the attachment portion is coupled to the leaflet window base.

15. A prosthetic heart valve, comprising:
a plurality of leaflets, wherein each leaflet includes a central region, a first side region on one side of the central region and a second side region on an opposite side of the central region, wherein the central region is defined by two central region sides, a leaflet base, and a leaflet free edge, wherein the leaflet base comprises a linear portion, wherein the two central region sides converge from the linear portion of the leaflet base toward the leaflet free edge, wherein the first side region is defined by a first one of the central region sides, a first leaflet side, and the leaflet free edge, wherein the second side region is defined by a second one of the central region sides, a second leaflet side, and the leaflet free edge, and wherein the first and second leaflet sides diverge from the linear portion of the leaflet base toward the leaflet free edge; and a frame having a plurality of spaced apart leaflet frame elements defining a plurality of leaflet windows, wherein each leaflet window comprises a leaflet window base and first and second leaflet window sides that diverge from the leaflet window base;

wherein one of the leaflets is located within each of the windows, wherein the first leaflet side is coupled along its length to the first leaflet window side and the second leaflet side is coupled along its length to the second leaflet window side, and wherein the leaflet base is coupled along its length to the leaflet window base.

16. The prosthetic heart valve of claim 15, wherein the length of the leaflet window base extends along a plane that that is transverse to a longitudinal axis of the frame.

17. The prosthetic heart valve of claim 15, wherein the leaflet base further comprises flat portion that is transverse relative to a longitudinal axis of the frame, wherein the flat portion extends from an attachment portion to the linear portion, and wherein the attachment portion is coupled to the leaflet window base.

18. A prosthetic heart valve, comprising:

a plurality of leaflets, wherein each leaflet includes a central region, a first side region on one side of the central region and a second side region on an opposite side of the central region, wherein the central region is defined by two central region sides, a leaflet base, and a leaflet free edge, wherein the leaflet base comprises a linear portion, wherein the two central region sides converge from the linear portion of the leaflet base toward the leaflet free edge, wherein the first side region is defined by a first one of the central region sides, a first leaflet side, and the leaflet free edge, wherein the second side region is defined by a second one of the central region sides, a second leaflet side, and the leaflet free edge, and wherein the first and second leaflet sides diverge from the linear portion of the leaflet base toward the leaflet free edge; and a frame having a plurality of spaced apart leaflet frame elements defining a plurality of leaflet windows, each leaflet window having one of the leaflets coupled thereto;

wherein the leaflets are moveable between an open position and a closed position; and wherein the central region of each leaflet is planar when the leaflets are in the closed position.

19. The prosthetic heart valve of claim 18, wherein each leaflet window comprises a leaflet window base and first and second leaflet window sides that diverge from the leaflet window base, and wherein a length of the leaflet window base extends along a plane that that is transverse to a longitudinal axis of the frame.

20. The prosthetic heart valve of claim 19, wherein the leaflet base further comprises flat portion that is transverse relative to a longitudinal axis of the frame, wherein the flat portion extends from an attachment portion to the linear portion, and wherein the attachment portion extends from the leaflet window base.

* * * * *